US006613746B1

(12) United States Patent
Seed et al.

(10) Patent No.: US 6,613,746 B1
(45) Date of Patent: **\*Sep. 2, 2003**

(54) AGP-ANTIBODY FUSION PROTEINS AND RELATED MOLECULES AND METHODS

(75) Inventors: Brian Seed, Boston, MA (US); Gerd Walz, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/472,888

(22) Filed: Jun. 7, 1995

Related U.S. Application Data

(63) Continuation-in-part of application No. 07/618,314, filed on Nov. 23, 1990, now abandoned.

(51) Int. Cl.⁷ ............................................. A01N 43/04
(52) U.S. Cl. .................. 514/23; 424/133.1; 424/134.1; 424/178.1; 435/972; 435/69.1; 530/387.1; 530/387.3; 530/395
(58) Field of Search ..................... 514/23, 2; 424/134.1, 424/178.1, 133.1; 435/972, 69.1; 530/387.3, 387.1, 395

(56) References Cited

U.S. PATENT DOCUMENTS

| 4,184,917 A | 1/1980 | Dorner et al. |
| 4,344,938 A | 8/1982 | Sedlacek et al. |
| 4,752,569 A | 6/1988 | Terasaki et al. |
| 4,816,567 A | 3/1989 | Cabilly et al. |
| 4,840,793 A | 6/1989 | Todd, III et al. |
| 4,851,511 A | 7/1989 | Hakomori et al. |
| 4,923,980 A | 5/1990 | Blomberg |
| 5,079,353 A | 1/1992 | Ratcliffe et al. |
| 5,143,712 A | 9/1992 | Brandley et al. |
| 5,211,936 A | 5/1993 | Brandley et al. |
| 5,225,538 A * | 7/1993 | Capon et al. ............ 530/387.3 |

FOREIGN PATENT DOCUMENTS

| EP | 0 146 090 | 6/1985 |
| EP | 0 218 257 | 4/1987 |
| EP | 0 251 304 | 1/1988 |
| EP | 0 314 863 | 5/1989 |
| EP | 0 319 253 | 6/1989 |
| EP | 0 323 802 | 7/1989 |
| GB | 1 550 914 | 8/1979 |
| WO | WO 89/08711 | 9/1989 |
| WO | WO 90/05539 | 5/1990 |
| WO | WO 90/05786 | 5/1990 |
| WO | WO 90/13300 | 11/1990 |
| WO | WO 91/16900 | 11/1991 |
| WO | WO 92/02527 | 2/1992 |

OTHER PUBLICATIONS

Biou et al. Biochem Biophys. Acta 913, 308–312, 1987.*
Walz, J. Am. Soc. Nephrol. 4:670 (Abstract # 81P), 1993.
Phillips et al., Science 250:1130–1132, 1990.
Walz et al., Science 250:1132–1135, 1990.
Fujiwara et al., J. Immunol. Meth. 112:77–83, 1988.
Stanley et al., J. Biol. Chem. 263 (23):11374–11382, 1988.
Fukushima et al., Cancer Res. 44:5279–5285, 1984.
Lowe et al., Cell 63:475–484, 1990.
Ghetie et al., Mol. Immunol. 23(4):377–384, 1986.
Fukuda et al., J. Biol. Chem. 259(17):10925–10935, 1984.
Johnson et al., Biochemical Society Transactions 15:396, 1987.
Aruffo et al., EMBO J. 6(11):3313–3316, 1987.
Seed et al., Proc. Natl. Acad. Sci. USA 84:3365–3369, 1987.
Aruffo et al., Proc. Natl. Acad. Sci USA 84:8573–8577, 1987.
Aruffo et al., Cell 61:1303–1313, 1990.
Bevilacqua et al., Science 243:1160, 1989.
Seed, Nature 329:840–842, 1987.
Lowe et al., Cell 63:475–484, 1990.
Okada et al., Clinica Chimica Acta 86:159–167 (1978).
Kijima–Suda et al., Cancer Res. 46:858–862, 1986.
Bowen et al., J. Cell Biol. 109:421–427, 1989.
Rice et al., Science 246:1303, 1989.
Stoolman, Cell 56:907–910, 1989.
Dobrina et al., Immunology 67:502–508, 1989.
Streeter et al., J. Cell Biol. 107:1853–1862, 1988.
Streeter et al., Nature 331:41–46, 1988.
Messadi et al., J. Immunol. 139(5):1557–1562, 1987.
Munro et al., Cytokine Interactions in Pathological Processes (8858–8863) p. A1821, No. 8862.
Pober et al., J. Immunol. 136(5):1680–1686, 1986.
Klein et al., Proc. Natl. Acad. Sci. USA 86:8972–8976, 1989.
Cotran et al., J. Exp. Med. 164:661–666, 1986.
Vedder et al., J. Clin. Invest. 81:939–944, 1988.
Jutila et al., Transplantation 48:727–731, 1989.
Simpson et al., J. Clin. Invest. 82:624–629, 1988.
Luscinskas et al., J. Immunol. 142:2257–2263, 1989.
Palcic et al., Carbohydrate Res. 190:1–11, 1989.
Masson et al., Clinica Chemica Acta 187:199–206, 1990.

(List continued on next page.)

Primary Examiner—Jennifer E. Graser
(74) Attorney, Agent, or Firm—Clark & Elbing LLP

(57) ABSTRACT

Disclosed is a method of inhibiting the binding of a cell bearing a cell adhesion protein to a molecule or cell bearing a carbohydrate determinant specific for the cell adhesion molecule. The method involves contacting the cell adhesion protein-bearing cell with an AGP-antibody bearing the carbohydrate determinant. Also disclosed are AGP-antibody fusion proteins to which are covalently bonded carbohydrate moieties which interfere with the antibody portion's ability to fix complement and bind an $F_c$ receptor. The methods of the invention may be used, for example, in any antibody-based therapy, for example, to reduce inflammation.

11 Claims, 19 Drawing Sheets

OTHER PUBLICATIONS

Herrero–Zabaleta et al., Bull. Cancer 74:387–396, 1987.
LePendu et al., Biochimie 70:1613–1617, 1988.
Mollicone et al., Blood 71(4):1113–1119, 1988.
Kuriyama et al., Biochim. Biophys. Acta 662:220–225, 1981.
Baker et al., Cancer Res. 47:2763–2766, 1987.
Arnaout et al., J. Cell Physiol. 137:305–309, 1988.
Hession et al., Proc. Natl. Acad. Sci. USA 87:1673–1677, 1990.
Ball et al., J. Immunol. 130(6):2937, 1983.
Hansson et al., J. Biol. Chem. 260(16):9388–9392, 1985.
Macher et al., J. Biol. Chem. 263(21):10186–10191, 1988.
Springer, Nature 346:425–434, 1990.
Zeittlmeisl, DNA Cell Biol. 9:349, 1990.
Libert, J. Exp. Med. 180:1571, 1994.

* cited by examiner

```
     AAGCTTACCACCATGGACTGGACCTGGAGGTTCCTCTTCTTTGTGGTGGCAGCAGCTACA
1    ---------+---------+---------+---------+---------+---------+  60
     TTCGAATGGTGGTACCTGACCTGGACCTCCAAGGAGAAGAAACACCACCGTCGTCGATGT

K  L  T  T  M  D  W  T  W  R  F  L  F  F  V  V  A  A  A  T     -

GGTGTCCAGTCCCAGGTGCAGCTGGTGCAGTCTGGGGCTGAGGTGAAGAAGCCTGGGTCC
61   ---------+---------+---------+---------+---------+---------+  120
     CCACAGGTCAGGGTCCACGTCGACCACGTCAGACCCCGACTCCACTTCTTCGGACCCAGG

G  V  Q  S  Q  V  Q  L  V  Q  S  G  A  E  V  K  K  P  G  S     -

TCGGTGAAGGTCTCCTGCAAGGCTTCTGGAGGCACCTTCAGCAGCTATGCTATCAGCTGG
121  ---------+---------+---------+---------+---------+---------+  180
     AGCCACTTCCAGAGGACGTTCCGAAGACCTCCGTGGAAGTCGTCGATACGATAGTCGACC

S  V  K  V  S  C  K  A  S  G  G  T  F  S  S  Y  A  I  S  W     -

GTGCGACAGGCCCCTGGACAAGGGCTTGAGTGGATGGGAGGGATCATCCCTATCTTTGGT
181  ---------+---------+---------+---------+---------+---------+  240
     CACGCTGTCCGGGGACCTGTTCCCGAACTCACCTACCCTCCCTAGTAGGGATAGAAACCA

V  R  Q  A  P  G  Q  G  L  E  W  M  G  G  I  I  P  I  F  G     -

ACAGCAAACTACGCACAGAAGTTCCAGGGCAGAGTCACGATTACCGCGGACGAATCCACG
241  ---------+---------+---------+---------+---------+---------+  300
     TGTCGTTTGATGCGTGTCTTCAAGGTCCCGTCTCAGTGCTAATGGCGCCTGCTTAGGTGC

T  A  N  Y  A  Q  K  F  Q  G  R  V  T  I  T  A  D  E  S  T     -

AGCACAGCCTACATGGAGCTGAGCAGCCTGAGATCTGAGGACACGGCCGTGTATTACTGT
301  ---------+---------+---------+---------+---------+---------+  360
     TCGTGTCGGATGTACCTCGACTCGTCGGACTCTAGACTCCTGTGCCGGCACATAATGACA

S  T  A  Y  M  E  L  S  S  L  R  S  E  D  T  A  V  Y  Y  C     -

GCGAGAGATAATGGAGCGTATTGTAGTGGTGGTAGCTGCTACTCGGGCTGGTTCGACCCC
361  ---------+---------+---------+---------+---------+---------+  420
     CGCTCTCTATTACCTCGCATAACATCACCACCATCGACGATGAGCCCGACCAAGCTGGGG

A  R  D  N  G  A  Y  C  S  G  G  S  C  Y  S  G  W  F  D  P     -

TGGGGCCAGGGAACCCTGGTCACCGTCTCTTCAGGTGAGTACTGAATTCTAGCTTTCTGG
421  ---------+---------+---------+---------+---------+---------+  480
     ACCCCGGTCCCTTGGGACCAGTGGCAGAGAAGTCCACTCATGACTTAAGATCGAAAGACC

```
              GGCAGGCCAGGCCTGACCTTGGCTTTGGGGCAGGGAGGGGGCTAAGGTGAGGCAGGTGGC
    481       ---------+---------+---------+---------+---------+---------+   540
              CCGTCCGGTCCGGACTGGAACCGAAACCCCGTCCCTCCCCCGATTCCACTCCGTCCACCG

GCCAGCAGGTGCACACCCAATGCCCATGAGCCCAGACACTGGACGCTGAACCTCGCGGAC
    541       ---------+---------+---------+---------+---------+---------+   600
              CGGTCGTCCACGTGTGGGTTACGGGTACTCGGGTCTGTGACCTGCGACTTGGAGCGCCTG

AGTTAAGAACCCAGGGGCCTCTGCGCCTGGGCCCAGCTCTGTCCCACACCGCGGTCACAT
    601       ---------+---------+---------+---------+---------+---------+   660
              TCAATTCTTGGGTCCCCGGAGACGCGGACCCGGGTCGAGACAGGGTGTGGCGCCAGTGTA

GGCACCACCTCTCTTGCAGCCTCCACCAAGGGCCCATCGGTCTTCCCCCTGGCACCCTCC
    661       ---------+---------+---------+---------+---------+---------+   720
              CCGTGGTGGAGAGAACGTCGGAGGTGGTTCCCGGGTAGCCAGAAGGGGGACCGTGGGAGG

A  S  T  K  G  P  S  V  F  P  L  A  P  S  -

TCCAAGAGCACCTCTGGGGGCACAGCGGCCCTGGGCTGCCTGGTCAAGGACTACTTCCCC
    721       ---------+---------+---------+---------+---------+---------+   780
              AGGTTCTCGTGGAGACCCCCGTGTCGCCGGGACCCGACGGACCAGTTCCTGATGAAGGGG

S  K  S  T  S  G  G  T  A  A  L  G  C  L  V  K  D  Y  F  P  -

GAACCGGTGACGGTGTCGTGGAACTCAGGCGCCCTGACCAGCGGCGTGCACACCTTCCCG
    781       ---------+---------+---------+---------+---------+---------+   840
              CTTGGCCACTGCCACAGCACCTTGAGTCCGCGGGACTGGTCGCCGCACGTGTGGAAGGGC

E  P  V  T  V  S  W  N  S  G  A  L  T  S  G  V  H  T  F  P  -

GCTGTCCTACAGTCCTCAGGACTCTACTCCCTCAGCAGCGTGGTGACCGTGCCCTCCAGC
    841       ---------+---------+---------+---------+---------+---------+   900
              CGACAGGATGTCAGGAGTCCTGAGATGAGGGAGTCGTCGCACCACTGGCACGGGAGGTCG

A  V  L  Q  S  S  G  L  Y  S  L  S  S  V  V  T  V  P  S  S  -

AGCTTGGGCACCCAGACCTACATCTGCAACGTGAATCACAAGCCCAGCAACACCAAGGTG
    901       ---------+---------+---------+---------+---------+---------+   960
              TCGAACCCGTGGGTCTGGATGTAGACGTTGCACTTAGTGTTCGGGTCGTTGTGGTTCCAC

S  L  G  T  Q  T  Y  I  C  N  V  N  H  K  P  S  N  T  K  V  -

GACAAGAAAGTTGGTGAGAGGCCAGCACAGGGAGGGAGGGTGTCTGCTGGAAGCAGGCTC
    961       ---------+---------+---------+---------+---------+---------+  1020
              CTGTTCTTTCAACCACTCTCCGGTCGTGTCCCTCCCTCCCACAGACGACCTTCGTCCGAG

```
       AGCGCTCCTGCCTGGACGCATCCCGGCTATGCAGCCCCAGTCCAGGGCAGCAAGGCAGGC
 1021  ---------+---------+---------+---------+---------+---------+ 1080
       TCGCGAGGACGGACCTGCGTAGGGCCGATACGTCGGGGTCAGGTCCCGTCGTTCCGTCCG

CCCGTCTGCCTCTTCACCCGGAGCCTCTGCCCGCCCCACTCATGCTCAGGGAGAGGGTCT
 1081  ---------+---------+---------+---------+---------+---------+ 1140
       GGGCAGACGGAGAAGTGGGCCTCGGAGACGGGCGGGGTGAGTACGAGTCCCTCTCCCAGA

TCTGGCTTTTTCCCAGGCTCTGGGCAGGCACAGGCTAGGTGCCCCTAACCCAGGCCCTGC
 1141  ---------+---------+---------+---------+---------+---------+ 1200
       AGACCGAAAAAGGGTCCGAGACCCGTCCGTGTCCGATCCACGGGGATTGGGTCCGGGACG

ACACAAAGGGGCAGGTGCTGGGCTCAGACCTGCCAAGAGCCATATCCGGGAGGACCCTGC
 1201  ---------+---------+---------+---------+---------+---------+ 1260
       TGTGTTTCCCCGTCCACGACCCGAGTCTGGACGGTTCTCGGTATAGGCCCTCCTGGGACG

CCCTGACCTAAGCCCACCCCAAAGGCCAAACTCTCCACTCCCTCAGCTCGGACACCTTCT
 1261  ---------+---------+---------+---------+---------+---------+ 1320
       GGGACTGGATTCGGGTGGGGTTTCCGGTTTGAGAGGTGAGGGAGTCGAGCCTGTGGAAGA

CTCCTCCCAGATTCCAGTAACTCCCAATCTTCTCTCTGCAGAGCCCAAATCTTGTGACAA
 1321  ---------+---------+---------+---------+---------+---------+ 1380
       GAGGAGGGTCTAAGGTCATTGAGGGTTAGAAGAGAGACGTCTCGGGTTTAGAACACTGTT

E   P   K   S   C   D   K   -

AACTCACACATGCCCACCGTGCCCAGGTAAGCCAGCCCAGGCCTCGCCCTCCAGCTCAAG
 1381  ---------+---------+---------+---------+---------+---------+ 1440
       TTGAGTGTGTACGGGTGGCACGGGTCCATTCGGTCGGGTCCGGAGCGGGAGGTCGAGTTC

T   H   T   C   P   P   C   P

GCGGGACAGGTGCCCTAGAGTAGCCTGCATCCAGGGACAGGCCCCAGCCGGGTGCTGACA
 1441  ---------+---------+---------+---------+---------+---------+ 1500
       CGCCCTGTCCACGGGATCTCATCGGACGTAGGTCCCTGTCCGGGGTCGGCCCACGACTGT

CGTCCACCTCCATCTCTTCCTCAGCACCTGAACTCCTGGGGGGACCGTCAGTCTTCCTCT
 1501  ---------+---------+---------+---------+---------+---------+ 1560
       GCAGGTGGAGGTAGAGAAGGAGTCGTGGACTTGAGGACCCCCCTGGCAGTCAGAAGGAGA

```
            TCCCCCCAAAACCCAAGGACACCCTCATGATCTCCCGGACCCCTGAGGTCACATGCGTGG
    1561    ---------+---------+---------+---------+---------+---------+    1620
            AGGGGGGTTTTGGGTTCCTGTGGGAGTACTAGAGGGCCTGGGGACTCCAGTGTACGCACC

P   P   K   P   K   D   T   L   M   I   S   R   T   P   E   V   T   C   V   V -

TGGTGGACGTGAGCCACGAAGACCCTGAGGTCAAGTTCAACTGGTACGTGGACGGCGTGG
    1621    ---------+---------+---------+---------+---------+---------+    1680
            ACCACCTGCACTCGGTGCTTCTGGGACTCCAGTTCAAGTTGACCATGCACCTGCCGCACC
                                                  N     S
              V   D   V   S   H   E   D   P   E   V   K   F   N   W   Y   V   D   G   V   E -
                                                  *   *   *   *   *   *   *   *           \
                                                 274                         281
                                                 (top)                       (bot)

AGGTGCATAATGCCAAGACAAAGCCGCGGGAGGAGCAGTACAACAGCACGTACCGGGTGG
    1681    ---------+---------+---------+---------+---------+---------+    1740
            TCCACGTATTACGGTTCTGTTTCGGCGCCCTCCTCGTCATGTTGTCGTGCATGGCCCACC
                    N                               N   S
              V   H   N   A   K   T   K   P   R   E   E   Q   Y   N   S   T   Y   R   V   V -
              \   \   \   \   \   \   X   X   X   /   /   /   #
                                     292         295 297
                                                     (top)

TCAGCGTCCTCACCGTCCTGCACCAGGACTGGCTGAATGGCAAGGAGTACAAGTGCAAGG
    1741    ---------+---------+---------+---------+---------+---------+    1800
            AGTCGCAGGAGTGGCAGGACGTGGTCCTGACCGACTTACCGTTCCTCATGTTCACGTTCC
                                                                          N
              S   V   L   T   V   L   H   Q   D   W   L   N   G   K   E   Y   K   C   K   V -
                                                              *       *       *
                                                             318     320     322

TCTCCAACAAAGCCCTCCCAGCCCCCATCGAGAAAACCATCTCCAAAGCCAAAGGTGGGA
    1801    ---------+---------+---------+---------+---------+---------+    1860
            AGAGGTTGTTTCGGGAGGGTCGGGGGTAGCTCTTTTGGTAGAGGTTTCGGTTTCCACCCT
                            N
              S   N   K   A   L   P   A   P   I   E   K   T   I   S   K   A   K
                                      *       *       *       *
                                     331     333     335     337

CCCGTGGGGTGCGAGGGCCACATGGACAGAGGCCGGCTCGGCCCACCCTCTGCCCTGAGA
    1861    ---------+---------+---------+---------+---------+---------+    1920
            GGGCACCCCACGCTCCCGGTGTACCTGTCTCCGGCCGAGCCGGGTGGGAGACGGGACTCT

GTGACCGCTGTACCAACCTCTGTCCTACAGGGCAGCCCCGAGAACCACAGGTGTACACCC
    1921    ---------+---------+---------+---------+---------+---------+    1980
            CACTGGCGACATGGTTGGAGACAGGATGTCCCGTCGGGGCTCTTGGTGTCCACATGTGGG

```
        TGCCCCCATCCCGGGATGAGCTGACCAAGAACCAGGTCAGCCTGACCTGCCTGGTCAAAG
1981    ---------+---------+---------+---------+---------+---------+ 2040
        ACGGGGGTAGGGCCCTACTCGACTGGTTCTTGGTCCAGTCGGACTGGACGGACCAGTTTC

P  P  S  R  D  E  L  T  K  N  Q  V  S  L  T  C  L  V  K  G -

GCTTCTATCCCAGCGACATCGCCGTGGAGTGGGAGAGCAATGGGCAGCCGGAGAACAACT
2041    ---------+---------+---------+---------+---------+---------+ 2100
        CGAAGATAGGGTCGCTGTAGCGGCACCTCACCCTCTCGTTACCCGTCGGCCTCTTGTTGA

F  Y  P  S  D  I  A  V  E  W  E  S  N  G  Q  P  E  N  N  Y -

ACAAGACCACGCCTCCCGTGCTGGACTCCGACGGCTCCTTCTTCCTCTACAGCAAGCTCA
2101    ---------+---------+---------+---------+---------+---------+ 2160
        TGTTCTGGTGCGGAGGGCACGACCTGAGGCTGCCGAGGAAGAAGGAGATGTCGTTCGAGT

K  T  T  P  P  V  L  D  S  D  G  S  F  F  L  Y  S  K  L  T -

CCGTGGACAAGAGCAGGTGGCAGCAGGGGAACGTCTTCTCATGCTCCGTGATGCATGAGG
2161    ---------+---------+---------+---------+---------+---------+ 2220
        GGCACCTGTTCTCGTCCACCGTCGTCCCCTTGCAGAAGAGTACGAGGCACTACGTACTCC

V  D  K  S  R  W  Q  Q  G  N  V  F  S  C  S  V  M  H  E  A -

CTCTGCACAACCACTACACGCAGAAGAGCCTCTCCCTGTCTCCGGGTAAATGAGTGCGAC
2221    ---------+---------+---------+---------+---------+---------+ 2280
        GAGACGTGTTGGTGATGTGCGTCTTCTCGGAGAGGGACAGAGGCCCATTTACTCACGCTG

L  H  N  H  Y  T  Q  K  S  L  S  L  S  P  G  K  *

GGCCGGC
2281    -------
        CCGGCCG
```

Fig. 1-5

| ADHESIVENESS | SCORE 1-5 |
|---|---|
| GRANULOCYTES | +++++ |
| HL-60 | ++++ |
| THP1 | ++++ |
| WIDR | ++ |
| U937 | (+) |
| HSB-2 | + |
Fig. 4
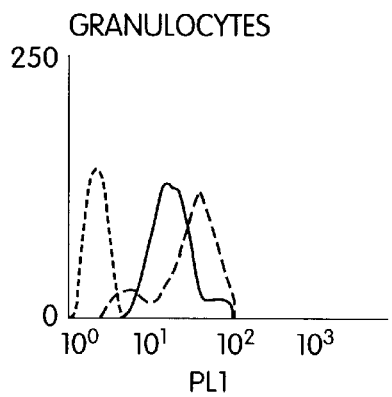
Fig. 5A
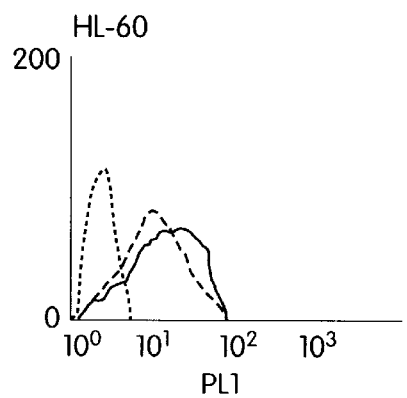
Fig. 5B
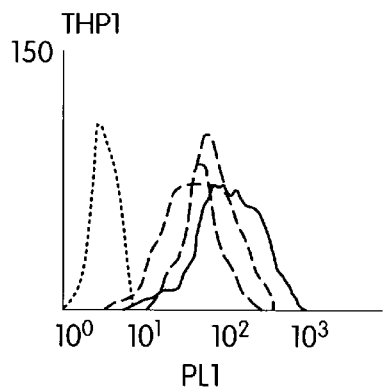
Fig. 5C
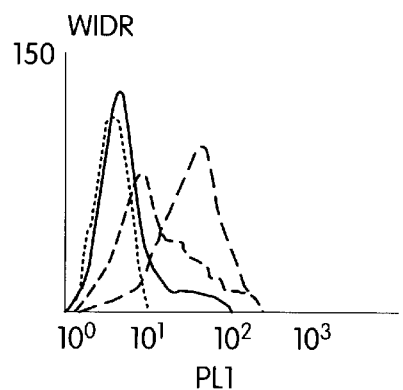
Fig. 5D
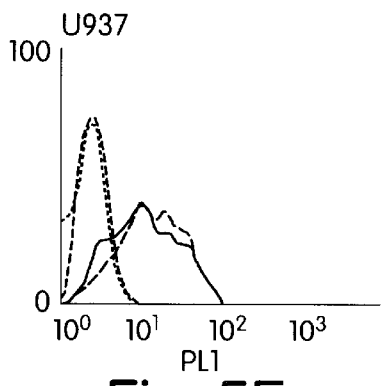
Fig. 5E
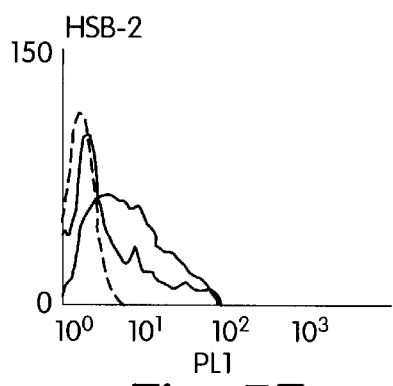
Fig. 5F ----------
          Agpeg1.

```
   1  ATGGCGCTGT CCTGGGTTCT TACAGTCCTG AGCCTCCTAC CTCTGCTGGA
  51  AGCCCAGATC CCATTGTGTG CCAACCTAGT ACCGGTGCCC ATCACCAACG
 101  CCACCCTGGA CCAGATCACT GGCAAGTGGT TTTATATCGC ATCGGCCTTT
 151  CGAAACGAGG AGTACAATAA GTCGGTTCAG GAGATCCAAG CAACCTTCTT
 201  TTACTTCACC CCCAACAAGA CAGAGGACAC GATCTTTCTC AGAGAGTACC
 251  AGACCCGACA GGACCAGTGC ATCTATAACA CCACCTACCT GAATGTCCAG
 301  CGGGAAAATG GGACCATCTC CAGATACGTG GGAGGCCAAG AGCATTTCGC
 351  TCACTTGCTG ATCCTCAGGG ACACCAAGAC CTACATGCTT GCTTTTGACG
 401  TGAACGATGA GAAGAACTGG GGGCTGTCTG TCTATGCTGA CAAGCCAGAG
 451  ACGACCAAGG AGCAACTGGG AGAGTTCTAC GAAGCTCTCG ACTGCTTGCG
 501  CATTCCCAAG TCAGATGTCG TGTACACCGA TTGGAAAAAG GATAAGTGTG
 551  AGCCACTGGA GAAGCAGCAC GAGAAGGAGA GGAAACAGGA GGAGGGGGAA
 601  TCGGATCCCG AGGGTGAGTA CTAAGCTTCA GCGCTCCTGC CTGGACGCAT
 651  CCCGGCTATG CAGCCCCAGT CCAGGGCAGC AAGGCAGGCC CCGTCTGCCT
 701  CTTCACCCGG AGCCTCTGCC CGCCCCACTC ATGCTCAGGG AGAGGGTCTT
 751  CTGGCTTTTT CCCAGGCTCT GGGCAGGCAC AGGCTAGGTG CCCCTAACCC
 801  AGGCCCTGCA CACAAGGGG CAGGTGCTGG GCTCAGACCT GCCAAGAGCC
 851  ATATCCGGGA GGACCCTGCC CCTGACCTAA GCCCACCCCA AAGGCCAAAC
 901  TCTCCACTCC CTCAGCTCGG ACACCTTCTC TCCTCCCAGA TTCCAGTAAC
 951  TCCCAATCTT CTCTCTGCAG AGCCCAAATC TTGTGACAAA ACTCACACAT
1001  GCCCACCGTG CCCAGGTAAG CCAGCCCAGG CCTCGCCCTC CAGCTCAAGG
1051  CGGGACAGGT GCCCTAGAGT AGCCTGCATC CAGGGACAGG CCCCAGCCGG
1101  GTGCTGACAC GTCCACCTCC ATCTCTTCCT CAGCACCTGA ACTCCTGGGG
1151  GGACCGTCAG TCTTCCTCTT CCCCCAAAA CCCAAGGACA CCCTCATGAT
```

Fig 15A-1

```
1201  CTCCCGGACC CCTGAGGTCA CATGCGTGGT GGTGGACGTG AGCCACGAAG
1251  ACCCTGAGGT CAAGTTCAAC TGGTACGTGG ACGGCGTGGA GGTGCATAAT
1301  GCCAAGACAA AGCCGCGGGA GGAGCAGTAC AACAGCACGT ACCGGGTGGT
1351  CAGCGTCCTC ACCGTCCTGC ACCAGGACTG GCTGAATGGC AAGGAGTACA
1401  AGTGCAAGGT CTCCAACAAA GCCCTCCCAG CCCCCATCGA GAAAACCATC
1451  TCCAAAGCCA AGGTGGGAC  CCGTGGGGTG CGAGGGCCAC ATGGACAGAG
1501  GCCGGCTCGG CCCACCCTCT GCCCTGAGAG TGACCGCTGT ACCAACCTCT
1551  GTCCTACAGG GCAGCCCCGA GAACCACAGG TGTACACCCT GCCCCCATCC
1601  CGGGATGAGC TGACCAAGAA CCAGGTCAGC CTGACCTGCC TGGTCAAAGG
1651  CTTCTATCCC AGCGACATCG CCGTGGAGTG GGAGAGCAAT GGGCAGCCGG
1701  AGAACAACTA CAAGACCACG CCTCCCGTGC TGGACTCCGA CGGCTCCTTC
1751  TTCCTCTACA GCAAGCTCAC CGTGGACAAG AGCAGGTGGC AGCAGGGGAA
1801  CGTCTTCTCA TGCTCCGTGA TGCATGAGGC TCTGCACAAC CACTACACGC
1851  AGAAGAGCCT CTCCCTGTCT CCGGGTAAAT GAGTGCGACG GCCG
```

Fig 15A-2    (SEQ ID NO: 3)

```
Agpeg1.Pep  Length: 438

1  MALSWVLTVL  SLLPLLEAQI  PLCANLVPVP  ITNATLDQIT  GKWFYIASAF
 51  RNEEYNKSVQ  EIQATFFYFT  PNKTEDTIFL  REYQTRQDQC  IYNTTYLNVQ
101  RENGTISRYV  GGQEHFAHLL  ILRDTKTYML  AFDVNDEKNW  GLSVYADKPE
151  TTKEQLGEFY  EALDCLRIPK  SDVVYTDWKK  DKCEPLEKQH  EKERKQEEGE
201  SDPEGEPKSC  DKTHTCPPCP  APELLGGPSV  FLFPPKPKDT  LMISRTPEVT
251  CVVVDVSHED  PEVKFNWYVD  GVEVHNAKTK  PREEQYNSTY  RVVSVLTVLH
301  QDWLNGKEYK  CKVSNKALPA  PIEKTISKAK  GQPREPQVYT  LPPSRDELTK
351  NQVSLTCLVK  GFYPSDIAVE  WESNGQPENN  YKTTPPVLDS  DGSFFLYSKL
401  TVDKSRWQQG  NVFSCSVMHE  ALHNHYTQKS  LSLSPGK*
```

Fig. 15B (SEQ ID NO: 4)

CD4 IgG1 DNA sequence

```
   1 GCCTGTTTGA GAAGCAGCGG GCAAGAAAGA CGCAAGCCCA GAGGCCCTGC
  51 CATTTCTGTG GGCTCAGGTC CCTACTGGCT CAGGCCCCTG CCTCCCTCGG
 101 CAAGGCCACA ATGAACCGGG GAGTCCCTTT TAGGCACTTG CTTCTGGTGC
 151 TGCAACTGGC GCTCCTCCCA GCAGCCACTC AGGGAAACAA AGTGGTGCTG
 201 GGCAAAAAAG GGGATACAGT GGAACTGACC TGTACAGCTT CCCAGAAGAA
 251 GAGCATACAA TTCCACTGGA AAAACTCCAA CCAGATAAAG ATTCTGGGAA
 301 ATCAGGGCTC CTTCTTAACT AAAGGTCCAT CCAAGCTGAA TGATCGCGCT
 351 GACTCAAGAA GAGCCTTTG GACCAAGGA ACTTCCCCC TGATCATCAA
 401 GAATCTTAAG ATAGAAGACT CAGATACTTA CATCTGTGAA GTGGAGGACC
 451 AGAAGGAGGA GGTGCAATTG CTAGTGTTCG GATTGACTGC AACTCTGAC
 501 ACCCACCTGC TTCAGGGGCA GAGCCTGACC CTGACCTTGG AGAGCCCCCC
 551 TGGTAGTAGC CCCTCAGTGC AATGTAGGAG TCCAAGGGGT AAAAACATAC
 601 AGGGGGGGAA GACCCTCTCC GTGTCTCAGC TGGAGCTCCA GGATAGTGGC
 651 ACCTGGACAT GCACTGTCTT GCAGAACCAG AAGAAGGTGG AGTTCAAAAT
 701 AGACATCGTG GTGCTAGCTT TCCAGAAGGC CTCCAGCATA GTCTATAAGA
 751 AAGAGGGGGA ACAGGTGGAG TTCTCCTTCC CACTCGCCTT TACAGTTGAA
 801 AAGCTGACGG GCAGTGGCGA GCTGTGGTGG CAGGCGGAGA GGGCTTCCTC
 851 CTCCAAGTCT TGGATCACCT TTGACCTGAA GAACAAGGAA GTGTCTGTAA
 901 AACGGGTTAC CCAGGACCCT AAGCTCCAGA TGGGCAAGAA GCTCCCGCTC
 951 CACCTCACCC TGCCCCAGGC CTTGCCTCAG TATGCTGGCT CTGGAAACCT
1001 CACCCTGGCC CTTGAAGCGA AAACAGGAAA GTTGCATCAG GAAGTGAACC
1051 TGGTGGTGAT GAGAGCCACT CAGCTCCAGA AAAATTTGAC CTGTGAGGTG
1101 TGGGGACCCA CCTCCCCTAA GCTGATGCTG AGCTTGAAAC TGGAGAACAA
1151 GGAGGCAAAG GTCTCGAAGC GGGAGAAGCC GGTGTGGGTG CTGAACCCTG
1201 AGGCGGGGAT GTGGCAGTGT CTGCTGAGTG ACTCGGGACA GGTCCTGCTG
1251 GAATCCAACA TCAAGGTTCT GCCCACATGG TCCACCCCGG TGCACGCGGA
```

Fig 16A-1

```
1301  TCCCGAGGGT GAGTACTAAG CTTCAGCGCT CCTGCCTGGA CGCATCCCGG
1351  CTATGCAGCC CCAGTCCAGG GCAGCAAGGC AGGCCCCGTC TGCCTCTTCA
1401  CCCGGAGCCT CTGCCCGCCC CACTCATGCT CAGGGAGAGG GTCTTCTGGC
1451  TTTTTCCCAG GCTCTGGGCA GGCACAGGCT AGGTGCCCCT AACCCAGGCC
1501  CTGCACACAA AGGGGCAGGT GCTGGGCTCA GACCTGCCAA GAGCCATATC
1551  CGGGAGGACC CTGCCCCTGA CCTAAGCCCA CCCCAAAGGC CAAACTCTCC
1601  ACTCCCTCAG CTCGGACACC TTCTCTCCTC CCAGATTCCA GTAACTCCCA
1651  ATCTTCTCTC TGCAGAGCCC AAATCTTGTG ACAAAACTCA CACATGCCCA
1701  CCGTGCCCAG GTAAGCCAGC CCAGGCCTCG CCCTCCAGCT CAAGGCGGGA
1751  CAGGTGCCCT AGAGTAGCCT GCATCCAGGG ACAGGCCCCA GCCGGGTGCT
1801  GACACGTCCA CCTCCATCTC TTCCTCAGCA CCTGAACTCC TGGGGGGACC
1851  GTCAGTCTTC CTCTTCCCCC CAAAACCCAA GGACACCCTC ATGATCTCCC
1901  GGACCCCTGA GGTCACATGC GTGGTGGTGG ACGTGAGCCA CGAAGACCCT
1951  GAGGTCAAGT TCAACTGGTA CGTGGACGGC GTGGAGGTGC ATAATGCCAA
2001  GACAAAGCCG CGGGAGGAGC AGTACAACAG CACGTACCGG GTGGTCAGCG
2051  TCCTCACCGT CCTGCACCAG GACTGGCTGA ATGGCAAGGA GTACAAGTGC
2101  AAGGTCTCCA ACAAAGCCCT CCCAGCCCCC ATCGAGAAAA CCATCTCCAA
2151  AGCCAAAGGT GGGACCCGTG GGGTGCGAGG GCCACATGGA CAGAGGCCGG
2201  CTCGGCCCAC CCTCTGCCCT GAGAGTGACC GCTGTACCAA CCTCTGTCCT
2251  ACAGGGCAGC CCCGAGAACC ACAGGTGTAC ACCCTGCCCC CATCCCGGGA
2301  TGAGCTGACC AAGAACCAGG TCAGCCTGAC CTGCCTGGTC AAAGGCTTCT
2351  ATCCCAGCGA CATCGCCGTG GAGTGGGAGA GCAATGGGCA GCCGGAGAAC
2401  AACTACAAGA CCACGCCTCC CGTGCTGGAC TCCGACGGCT CCTTCTTCCT
2451  CTACAGCAAG CTCACCGTGG ACAAGAGCAG GTGGCAGCAG GGGAACGTCT
2501  TCTCATGCTC CGTGATGCAT GAGGCTCTGC ACAACCACTA CACGCAGAAG
2551  AGCCTCTCCC TGTCTCCGGG TAAATGAGTG CGACGGCCG
```

Fig 16A-2   (SEQ ID NO: 5)

CD4 IgG1 fusion protein polypeptide.

```
  1  MNRGVPFRHL  LLVLQLALLP  AATQGNKVVL  GKKGDTVELT  CTASQKKSIQ
 51  FHWKNSNQIK  ILGNQGSFLT  KGPSKLNDRA  DSRRSLWDQG  NFPLIIKNLK
101  IEDSDTYICE  VEDQKEEVQL  LVFGLTANSD  THLLQGQSLT  LTLESPPGSS
151  PSVQCRSPRG  KNIQGGKTLS  VSQLELQDSG  TWTCTVLQNQ  KKVEFKIDIV
201  VLAFQKASSI  VYKKEGEQVE  FSFPLAFTVE  KLTGSGELWW  QAERASSSKS
251  WITFDLKNKE  VSVKRVTQDP  KLQMGKKLPL  HLTLPQALPQ  YAGSGNLTLA
301  LEAKTGKLHQ  EVNLVVMRAT  QLQKNLTCEV  WGPTSPKLML  SLKLENKEAK
351  VSKREKPVWV  LNPEAGMWQC  LLSDSGQVLL  ESNIKVLPTW  STPVHADPEG
401  EPKSCDKTHT  CPPCPAPELL  GGPSVFLFPP  KPKDTLMISR  TPEVTCVVVD
451  VSHEDPEVKF  NWYVDGVEVH  NAKTKPREEQ  YNSTYRVVSV  LTVLHQDWLN
501  GKEYKCKVSN  KALPAPIEKT  ISKAKGQPRE  PQVYTLPPSR  DELTKNQVSL
551  TCLVKGFYPS  DIAVEWESNG  QPENNYKTTP  PVLDSDGSFF  LYSKLTVDKS
601  RWQQGNVFSC  SVMHEALHNH  YTQKSLSLSP  GK*
```

Fig. 16B (SEQ ID NO: 6)

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 2287 base pairs
        (B) TYPE: nucleic acid
        (C) STRANDEDNESS: double
        (D) TOPOLOGY: linear (ii) MOLECULE TYPE: Genomic DNA (ix) FEATURE:
        (A) NAME/KEY: Coding Sequence
        (B) LOCATION: 1...300, 361...453, 679...903, 961...972,
            1360...1404, 1524...1853, 1950...2270
        (D) OTHER INFORMATION:

(xi) SEQUENCE DESCRIPTION: SEQ ID NO:1:

```
AAG CTT ACC ACC ATG GAC TGG ACC TGG AGG TTC CTC TTC TTT GTG GTG        48
Lys Leu Thr Thr Met Asp Trp Thr Trp Arg Phe Leu Phe Phe Val Val
                 5                  10                  15

GCA GCA GCT ACA GGT GTC CAG TCC CAG GTG CAG CTG GTG CAG TCT GGG        96
Ala Ala Ala Thr Gly Val Gln Ser Gln Val Gln Leu Val Gln Ser Gly
         20                  25                  30

GCT GAG GTG AAG AAG CCT GGG TCC TCG GTG AAG GTC TCC TGC AAG GCT       144
Ala Glu Val Lys Lys Pro Gly Ser Ser Val Lys Val Ser Cys Lys Ala
     35                  40                  45

TCT GGA GGC ACC TTC AGC AGC TAT GCT ATC AGC TGG GTG CGA CAG GCC       192
Ser Gly Gly Thr Phe Ser Ser Tyr Ala Ile Ser Trp Val Arg Gln Ala
 50                  55                  60

CCT GGA CAA GGG CTT GAG TGG ATG GGA GGG ATC ATC CCT ATC TTT GGT       240
Pro Gly Gln Gly Leu Glu Trp Met Gly Gly Ile Ile Pro Ile Phe Gly
 65                  70                  75                  80

ACA GCA AAC TAC GCA CAG AAG TTC CAG GGC AGA GTC ACG ATT ACC GCG       288
Thr Ala Asn Tyr Ala Gln Lys Phe Gln Gly Arg Val Thr Ile Thr Ala
             85                  90                  95

GAC GAA TCC ACG                                                       300
Asp Glu Ser Thr
             100

AGCACAGCCT ACATGGAGCT GAGCAGCCTG AGATCTGAGG ACACGGCCGT GTATTACTGT     360

GCG AGA GAT AAT GGA GCG TAT TGT AGT GGT GGT AGC TGC TAC TCG GGC       408
Ala Arg Asp Asn Gly Ala Tyr Cys Ser Gly Gly Ser Cys Tyr Ser Gly
                 105                 110                 115

TGG TTC GAC CCC TGG GGC CAG GGA ACC CTG GTC ACC GTC TCT TCA           453
Trp Phe Asp Pro Trp Gly Gln Gly Thr Leu Val Thr Val Ser Ser
             120                 125                 130

GGTGAGTACT GAATTCTAGC TTTCTGGGGC AGGCCAGGCC TGACCTTGGC TTTGGGGCAG     513

GGAGGGGGCT AAGGTGAGGC AGGTGGCGCC AGCAGGTGCA CACCCAATGC CCATGAGCCC     573
```

```
AGACACTGGA CGCTGAACCT CGCGGACAGT TAAGAACCCA GGGGCCTCTG CGCCTGGGCC    633

CAGCTCTGTC CCACACCGCG GTCACATGGC ACCACCTCTC TTGCA                   678

GCC TCC ACC AAG GGC CCA TCG GTC TTC CCC CTG GCA CCC TCC TCC AAG    726
Ala Ser Thr Lys Gly Pro Ser Val Phe Pro Leu Ala Pro Ser Ser Lys
            135                 140                 145

AGC ACC TCT GGG GGC ACA GCG GCC CTG GGC TGC CTG GTC AAG GAC TAC    774
Ser Thr Ser Gly Gly Thr Ala Ala Leu Gly Cys Leu Val Lys Asp Tyr
            150                 155                 160

TTC CCC GAA CCG GTG ACG GTG TCG TGG AAC TCA GGC GCC CTG ACC AGC    822
Phe Pro Glu Pro Val Thr Val Ser Trp Asn Ser Gly Ala Leu Thr Ser
    165                 170                 175

GGC GTG CAC ACC TTC CCG GCT GTC CTA CAG TCC TCA GGA CTC TAC TCC    870
Gly Val His Thr Phe Pro Ala Val Leu Gln Ser Ser Gly Leu Tyr Ser
180                 185                 190                 195

CTC AGC AGC GTG GTG ACC GTG CCC TCC AGC AGC                         903
Leu Ser Ser Val Val Thr Val Pro Ser Ser Ser
                    200                 205

TTGGGCACCC AGACCTACAT CTGCAACGTG AATCACAAGC CCAGCAACAC CAAGGTG      960

GAC AAG AAA GTT                                                     972
Asp Lys Lys Val
            210

GGTGAGAGGC CAGCACAGGG AGGGAGGGTG TCTGCTGGAA GCAGGCTCAG CGCTCCTGCC  1032

TGGACGCATC CCGGCTATGC AGCCCCAGTC CAGGGCAGCA AGGCAGGCCC CGTCTGCCTC  1092

TTCACCCGGA GCCTCTGCCC GCCCCACTCA TGCTCAGGGA GAGGGTCTTC TGGCTTTTTC  1152

CCAGGCTCTG GGCAGGCACA GGCTAGGTGC CCCTAACCCA GGCCCTGCAC ACAAAGGGGC  1212

AGGTGCTGGG CTCAGACCTG CCAAGAGCCA TATCCGGGAG GACCCTGCCC CTGACCTAAG  1272

CCCACCCCAA AGGCCAAACT CTCCACTCCC TCAGCTCGGA CACCTTCTCT CCTCCCAGAT  1332

TCCAGTAACT CCCAATCTTC TCTCTGC                                     1359

AGA GCC CAA ATC TTG TGA CAA AAC TCA CAC ATG CCC ACC GTG CCC       1404
Glu Pro Lys Ser Cys Asp Lys Thr His Thr Cys Pro Pro Cys Pro
                215                 220                 225

AGGTAAGCCA GCCCAGGCCT CGCCCTCCAG CTCAAGGCGG GACAGGTGCC CTAGAGTAGC  1464

CTGCATCCAG GGACAGGCCC CAGCCGGGTG CTGACACGTC CACCTCCATC TCTTCCTCA   1523

GCA CCT GAA CTC CTG GGG GGA CCG TCA GTC TTC CTC TAG GGG GGT TTT   1571
Ala Pro Glu Leu Leu Gly Gly Pro Ser Val Phe Leu Phe Pro Pro Lys
                230                 235                 240

GGG TTC CTG TGG GAG TAC TAG AGG GCC TGG GGA CTC CAG TGT ACG CAC   1619
Pro Lys Asp Thr Leu Met Ile Ser Arg Thr Pro Glu Val Thr Cys Val
            245                 250                 255

CTG GTG GAC GTG AGC CAC GAA GAC CCT GAG GTC AAG TTC AAC TGG TAC   1667
Val Val Asp Val Ser His Glu Asp Pro Glu Val Lys Phe Asn Trp Tyr
            260                 265                 270

GTG GAC GGC GTG GAG GTG CAT AAT GCC AAG ACA AAG CCG CGG GAG GAG   1715
Val Asp Gly Val Glu Val His Asn Ala Lys Thr Lys Pro Arg Glu Glu
    275                 280                 285

CAG TAC AAC AGC ACG TAC CGG GTG GTC AGC GTC CTC ACC GTC CTG CAC   1763
Gln Tyr Asn Ser Thr Tyr Arg Val Val Ser Val Leu Thr Val Leu His
290                 295                 300                 305

CAG GAC TGG CTG AAT GGC AAG GAG TAC AAG TGC AAG GTC TCC AAC AAA   1811
Gln Asp Trp Leu Asn Gly Lys Glu Tyr Lys Cys Lys Val Ser Asn Lys
            310                 315                 320

GCC CTC CCA GCC CCC ATC GAG AAA ACC ATC TCC AAA GCC AAA           1853
Ala Leu Pro Ala Pro Ile Glu Lys Thr Ile Ser Lys Ala Lys
                325                 330                 335
```

-continued

```
GGTGGGACCC GTGGGGTGCG AGGGCCACAT GGACAGAGGC CGGCTCGGCC CACCCTCT        1911

GCCCTGAGAG TGACCGCTGT ACCAACCTCT GTCCTACA                              1949

GGG CAG CCC CGA GAA CCA CAG GTG TAC ACC CTG CCC CCA TCC CGG GAT        1997
Gly Gln Pro Arg Glu Pro Gln Val Tyr Thr Leu Pro Pro Ser Arg Asp
            340                 345                 350

GAG CTG ACC AAG AAC CAG GTC AGC CTG ACC TGC CTG GTC AAA GGC TTC        2045
Glu Leu Thr Lys Asn Gln Val Ser Leu Thr Cys Leu Val Lys Gly Phe
            355                 360                 365

TAT CCC AGC GAC ATC GCC GTG GAG TGG GAG AGC AAT GGG CAG CCG GAG        2093
Tyr Pro Ser Asp Ile Ala Val Glu Trp Glu Ser Asn Gly Gln Pro Glu
            370                 375                 380

AAC AAC TAC AAG ACC ACG CCT CCC GTG CTG GAC TCC GAC GGC TCC TTC        2141
Asn Asn Tyr Lys Thr Thr Pro Pro Val Leu Asp Ser Asp Gly Ser Phe
385                 390                 395

TTC CTC TAC AGC AAG CTC ACC GTG GAC AAG AGC AGG TGG CAG CAG GGG        2189
Phe Leu Tyr Ser Lys Leu Thr Val Asp Lys Ser Arg Trp Gln Gln Gly
400                 405                 410                 415

AAC GTC TTC TCA TGC TCC GTG ATG CAT GAG GCT CTG CAC AAC CAC TAC        2237
Asn Val Phe Ser Cys Ser Val Met His Glu Ala Leu His Asn His Tyr
            420                 425                 430

ACG CAG AAG AGC CTC TCC CTG TCT CCG GGT AAA                            2270
Thr Gln Lys Ser Leu Ser Leu Ser Pro Gly Lys
            435                 440

TGAGTGCGAC GGCCGGC                                                     2287
```

(2) INFORMATION FOR SEQ ID NO:2:

(i) SEQUENCE CHARACTERISTICS:
        (A) LENGTH: 442 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:2:

```
Lys Leu Thr Thr Met Asp Trp Thr Trp Arg Phe Leu Phe Val Val
1               5                   10                  15

Ala Ala Ala Thr Gly Val Gln Ser Gln Val Gln Leu Val Gln Ser Gly
            20                  25                  30

Ala Glu Val Lys Lys Pro Gly Ser Ser Val Lys Val Ser Cys Lys Ala
            35                  40                  45

Ser Gly Gly Thr Phe Ser Ser Tyr Ala Ile Ser Trp Val Arg Gln Ala
    50                  55                  60

Pro Gly Gln Gly Leu Glu Trp Met Gly Gly Ile Ile Pro Ile Phe Gly
65                  70                  75                  80

Thr Ala Asn Tyr Ala Gln Lys Phe Gln Gly Arg Val Thr Ile Thr Ala
                85                  90                  95

Asp Glu Ser Thr Ala Arg Asp Asn Gly Ala Tyr Cys Ser Gly Gly Ser
            100                 105                 110

Cys Tyr Ser Gly Trp Phe Asp Pro Trp Gly Gln Gly Thr Leu Val Thr
        115                 120                 125

Val Ser Ser Ala Ser Thr Lys Gly Pro Ser Val Phe Pro Leu Ala Pro
        130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
```

```
                        165                 170                 175
Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Asp Lys
            195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Asn Phe Ser Trp
            260                 265                 270

Tyr Val Asp Gly Val Glu Val His Asn Asn Lys Thr Lys Pro Arg Glu
        275                 280                 285

Glu Asn Tyr Ser Ser Thr Tyr Arg Val Val Ser Val Leu Thr Val Leu
290                 295                 300

His Gln Asp Trp Leu Asn Gly Lys Glu Tyr Lys Cys Asn Val Ser Asn
305                 310                 315                 320

Lys Ala Leu Pro Ala Pro Ile Glu Lys Asn Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

(2) INFORMATION FOR SEQ ID NO:3:

(i) SEQUENCE CHARACTERISTICS:
        (A) LENGTH: 1894 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

ATGGCGCTGT CCTGGGTTCT TACAGTCCTG AGCCTCCTAC CTCTGCTGGA AGCCCAGATC      60

CCATTGTGTG CCAACCTAGT ACCGGTGCCC ATCACCAACG CCACCCTGGA CCAGATCACT     120

GGCAAGTGGT TTTATATCGC ATCGGCCTTT CGAAACGAGG AGTACAATAA GTCGGTTCAG     180

GAGATCCAAG CAACCTTCTT TTACTTCACC CCCAACAAGA CAGAGGACAC GATCTTTCTC     240

AGAGAGTACC AGACCCGACA GGACCAGTGC ATCTATAACA CCACCTACCT GAATGTCCAG     300

CGGGAAAATG GGACCATCTC CAGATACGTG GGAGGCCAAG AGCATTTCGC TCACTTGCTG     360

ATCCTCAGGG ACACCAAGAC CTACATGCTT GCTTTTGACG TGAACGATGA AAAGAACTGG     420
```

```
GGGCTGTCTG TCTATGCTGA CAAGCCAGAG ACGACCAAGG AGCAACTGGG AGAGTTCTAC      480

GAAGCTCTCG ACTGCTTGCG CATTCCCAAG TCAGATGTCG TGTACACCGA TTGGAAAAAG      540

GATAAGTGTG AGCCACTGGA GAAGCAGCAC GAGAAGGAGA GGAAACAGGA GGAGGGGGAA      600

TCGGATCCCG AGGGTGAGTA CTAAGCTTCA GCGCTCCTGC CTGGACGCAT CCCGGCTATG      660

CAGCCCCAGT CCAGGGCAGC AAGGCAGGCC CCGTCTGCCT CTTCACCCGG AGCCTCTGCC      720

CGCCCCACTC ATGCTCAGGG AGAGGGTCTT CTGGCTTTTT CCCAGGCTCT GGGCAGGCAC      780

AGGCTAGGTG CCCCTAACCC AGGCCCTGCA CACAAAGGGG CAGGTGCTGG GCTCAGACCT      840

GCCAAGAGCC ATATCCGGGA GGACCCTGCC CCTGACCTAA GCCCACCCCA AAGGCCAAAC      900

TCTCCACTCC CTCAGCTCGG ACACCTTCTC TCCTCCCAGA TTCCAGTAAC TCCCAATCTT      960

CTCTCTGCAG AGCCCAAATC TTGTGACAAA ACTCACACAT GCCCACCGTG CCCAGGTAAG     1020

CCAGCCCAGG CCTCGCCCTC CAGCTCAAGG CGGGACAGGT GCCCTAGAGT AGCCTGCATC     1080

CAGGGACAGG CCCCAGCCGG GTGCTGACAC GTCCACCTCC ATCTCTTCCT CAGCACCTGA     1140

ACTCCTGGGG GGACCGTCAG TCTTCCTCTT CCCCCCAAAA CCCAAGGACA CCCTCATGAT     1200

CTCCCGGACC CCTGAGGTCA CATGCGTGGT GGTGGACGTG AGCCACGAAG ACCCTGAGGT     1260

CAAGTTCAAC TGGTACGTGG ACGGCGTGGA GGTGCATAAT GCCAAGACAA AGCCGCGGGA     1320

GGAGCAGTAC AACAGCACGT ACCGGGTGGT CAGCGTCCTC ACCGTCCTGC ACCAGGACTG     1380

GCTGAATGGC AAGGAGTACA AGTGCAAGGT CTCCAACAAA GCCCTCCCAG CCCCCATCGA     1440

GAAAACCATC TCCAAAGCCA AGGTGGGAC CCGTGGGGTG CGAGGGCCAC ATGGACAGAG     1500

GCCGGCTCGG CCCACCCTCT GCCCTGAGAG TGACCGCTGT ACCAACCTCT GTCCTACAGG     1560

GCAGCCCCGA GAACCACAGG TGTACACCCT GCCCCCATCC CGGGATGAGC TGACCAAGAA     1620

CCAGGTCAGC CTGACCTGCC TGGTCAAAGG CTTCTATCCC AGCGACATCG CCGTGGAGTG     1680

GGAGAGCAAT GGGCAGCCGG AGAACAACTA CAAGACCACG CCTCCCGTGC TGGACTCCGA     1740

CGGCTCCTTC TTCCTCTACA GCAAGCTCAC CGTGGACAAG AGCAGGTGGC AGCAGGGGAA     1800

CGTCTTCTCA TGCTCCGTGA TGCATGAGGC TCTGCACAAC CACTACACGC AGAAGAGCCT     1860

CTCCCTGTCT CCGGGTAAAT GAGTGCGACG GCCG                                 1894
```

(2) INFORMATION FOR SEQ ID NO:4:

(i) SEQUENCE CHARACTERISTICS:
        (A) LENGTH: 434 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:4:

```
Met Ala Leu Ser Trp Val Leu Thr Val Leu Ser Leu Leu Pro Leu Leu
 1               5                  10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80
```

```
Arg Glu Tyr Gln Thr Arg Gln Asp Gln Cys Ile Tyr Asn Thr Thr Tyr
                 85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Trp Tyr Thr Asp
                165                 170                 175

Trp Lys Lys Asp Lys Cys Glu Pro Leu Glu Lys Gln His Glu Lys Glu
            180                 185                 190

Arg Lys Gln Glu Glu Gly Glu Ser Asp Pro Glu Gly Glu Pro Lys Ser
        195                 200                 205

Cys Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Asp Glu Leu Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys
```

(2) INFORMATION FOR SEQ ID NO:5:

(i) SEQUENCE CHARACTERISTICS:
        (A) LENGTH: 2589 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
GCCTGTTTGA AAGCAGCGG GCAAGAAAGA CGCAAGCCCA GAGGCCCTGC CATTTCTGTG        60
GGCTCAGGTC CCTACTGGCT CAGGCCCCTG CCTCCCTCGG CAAGGCCACA ATGAACCGGG       120
GAGTCCCTTT TAGGCACTTG CTTCTGGTGC TGCAACTGGC GCTCCTCCCA GCAGCCACTC       180
AGGGAAACAA AGTGGTGCTG GGCAAAAAAG GGGATACAGT GGAACTGACC TGTACAGCTT       240
CCCAGAAGAA GAGCATACAA TTCCACTGGA AAAACTCCAA CCAGATAAAG ATTCTGGGAA       300
ATCAGGGCTC CTTCTTAACT AAAGGTCCAT CCAAGCTGAA TGATCGCGCT GACTCAAGAA       360
GAAGCCTTTG GGACCAAGGA AACTTCCCCC TGATCATCAA GAATCTTAAG ATAGAAGACT       420
CAGATACTTA CATCTGTGAA GTGGAGGACC AGAAGGAGGA GGTGCAATTG CTAGTGTTCG       480
GATTGACTGC CAACTCTGAC ACCCACCTGC TTCAGGGCA GAGCCTGACC CTGACCTTGG        540
AGAGCCCCCC TGGTAGTAGC CCCTCAGTGC AATGTAGGAG TCCAAGGGGT AAAAACATAC       600
AGGGGGGAA GACCCTCTCC GTGTCTCAGC TGGAGCTCCA GGATAGTGGC ACCTGGACAT        660
GCACTGTCTT GCAGAACCAG AAGAAGGTGG AGTTCAAAAT AGACATCGTG GTGCTAGCTT       720
TCCAGAAGGC CTCCAGCATA GTCTATAAGA AAGAGGGGA ACAGGTGGAG TTCTCCTTCC        780
CACTCGCCTT TACAGTTGAA AAGCTGACGG GCAGTGGCGA GCTGTGGTGG CAGGCGGAGA       840
GGGCTTCCTC CTCCAAGTCT TGGATCACCT TTGACCTGAA GAACAAGGAA GTGTCTGTAA       900
AACGGGTTAC CCAGGACCCT AAGCTCCAGA TGGGCAAGAA GCTCCCGCTC CACCTCACCC       960
TGCCCCAGGC CTTGCCTCAG TATGCTGGCT CTGGAAACCT CACCCTGGCC CTTGAAGCGA      1020
AAACAGGAAA GTTGCATCAG GAAGTGAACC TGGTGGTGAT GAGAGCCACT CAGCTCCAGA      1080
AAAATTTGAC CTGTGAGGTG TGGGGACCCA CCTCCCCTAA GCTGATGCTG AGCTTGAAAC      1140
TGGAGAACAA GGAGGCAAAG GTCTCGAAGC GGGAGAAGCC GGTGTGGGTG CTGAACCCTG      1200
AGGCGGGGAT GTGGCAGTGT CTGCTGAGTG ACTCGGGACA GGTCCTGCTG AATCCAACA       1260
TCAAGGTTCT GCCCACATGG TCCACCCCGG TGCACGCGGA TCCCGAGGGT GAGTACTAAG      1320
CTTCAGCGCT CCTGCCTGGA CGCATCCCGG CTATGCAGCC CCAGTCCAGG GCAGCAAGGC      1380
AGGCCCCGTC TGCCTCTTCA CCCGGAGCCT CTGCCCGCCC CACTCATGCT CAGGGAGAGG      1440
GTCTTCTGGC TTTTTCCCAG GCTCTGGGCA GGCACAGGCT AGGTGCCCCT AACCCAGGCC      1500
CTGCACACAA AGGGGCAGGT GCTGGGCTCA GACCTGCCAA GAGCCATATC CGGGAGGACC      1560
CTGCCCCTGA CCTAAGCCCA CCCCAAAGGC CAAACTCTCC ACTCCCTCAG CTCGGACACC      1620
TTCTCTCCTC CCAGATTCCA GTAACTCCCA ATCTTCTCTC TGCAGAGCCC AAATCTTGTG      1680
ACAAAACTCA CACATGCCCA CCGTGCCCAG GTAAGCCAGC CCAGGCCTCG CCCTCCAGCT      1740
CAAGGCGGGA CAGGTGCCCT AGAGTAGCCT GCATCCAGGG ACAGGCCCCA GCCGGGTGCT      1800
GACACGTCCA CCTCCATCTC TTCCTCAGCA CCTGAACTCC TGGGGGGACC GTCAGTCTTC      1860
CTCTTCCCCC CAAAACCCAA GGACACCCTC ATGATCTCCC GGACCCCTGA GGTCACATGC      1920
GTGGTGGTGG ACGTGAGCCA CGAAGACCCT GAGGTCAAGT TCAACTGGTA CGTGGACGGC      1980
GTGGAGGTGC ATAATGCCAA GACAAAGCCG CGGGAGGAGC AGTACAACAG CACGTACCGG      2040
GTGGTCAGCG TCCTCACCGT CCTGCACCAG GACTGGCTGA ATGGCAAGGA GTACAAGTGC      2100
AAGGTCTCCA ACAAAGCCCT CCCAGCCCCC ATCGAGAAAA CCATCTCCAA AGCCAAAGGT      2160
GGGACCCGTG GGGTGCGAGG GCCACATGGA CAGAGGCCGG CTCGGCCCAC CCTCTGCCCT      2220
GAGAGTGACC GCTGTACCAA CCTCTGTCCT ACAGGGCAGC CCCGAGAACC ACAGGTGTAC      2280
ACCCTGCCCC CATCCCGGGA TGAGCTGACC AAGAACCAGG TCAGCCTGAC CTGCCTGGTC      2340
```

```
AAAGGCTTCT ATCCCAGCGA CATCGCCGTG GAGTGGGAGA GCAATGGGCA GCCGGAGAAC   2400

AACTACAAGA CCACGCCTCC CGTGCTGGAC TCCGACGGCT CCTTCTTCCT CTACAGCAAG   2460

CTCACCGTGG ACAAGAGCAG GTGGCAGCAG GGAACGTCT  TCTCATGCTC CGTGATGCAT   2520

GAGGCTCTGC ACAACCACTA CACGCAGAAG AGCCTCTCCC TGTCTCCGGG TAAATGAGTG   2580

CGACGGCCG                                                          2589
```

(2) INFORMATION FOR SEQ ID NO:6:

(i) SEQUENCE CHARACTERISTICS:
        (A) LENGTH: 630 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:6:

```
Met Asn Arg Gly Val Pro Phe Arg His Leu Leu Leu Val Leu Gln Leu
 1               5                  10                  15

Ala Leu Leu Pro Ala Ala Thr Gln Gly Asn Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
```

-continued

```
            290                 295                 300
Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Pro Val Trp Val Leu Asn Pro Glu Ala Gly Met Trp
            355                 360                 365

Gln Cys Leu Leu Ser Asp Ser Gly Gln Val Leu Leu Glu Ser Asn Ile
        370                 375                 380

Lys Val Leu Pro Thr Trp Ser Thr Pro Val His Ala Asp Pro Glu Gly
385                 390                 395                 400

Glu Pro Lys Ser Cys Asp Lys Thr His Thr Cys Pro Pro Cys Pro Ala
                405                 410                 415

Pro Glu Leu Leu Gly Gly Pro Ser Val Phe Leu Phe Pro Pro Lys Pro
                420                 425                 430

Lys Asp Thr Leu Met Ile Ser Arg Thr Pro Glu Val Thr Cys Trp Val
                435                 440                 445

Asp Val Ser His Glu Asp Pro Glu Val Lys Phe Asn Trp Tyr Val Asp
450                 455                 460

Gly Val Glu Val His Asn Ala Lys Thr Lys Pro Arg Glu Glu Gln Tyr
465                 470                 475                 480

Asn Ser Thr Tyr Arg Trp Ser Val Leu Thr Val Leu His Gln Asp Trp
                485                 490                 495

Leu Asn Gly Lys Glu Tyr Lys Cys Lys Val Ser Asn Lys Ala Leu Pro
            500                 505                 510

Ala Pro Ile Glu Lys Thr Ile Ser Lys Ala Lys Gly Gln Pro Arg Glu
            515                 520                 525

Pro Gln Val Tyr Thr Leu Pro Pro Ser Arg Asp Glu Leu Thr Lys Asn
            530                 535                 540

Gln Val Ser Leu Thr Cys Leu Val Lys Gly Phe Tyr Pro Ser Asp Ile
545                 550                 555                 560

Ala Val Glu Trp Glu Ser Asn Gly Gln Pro Glu Asn Asn Tyr Lys Thr
                565                 570                 575

Thr Pro Pro Val Leu Asp Ser Asp Gly Ser Phe Phe Leu Tyr Ser Lys
                580                 585                 590

Leu Thr Val Asp Lys Ser Arg Trp Gln Gln Gly Asn Val Phe Ser Cys
            595                 600                 605

Ser Val Met His Glu Ala Leu His Asn His Tyr Thr Gln Lys Ser Leu
            610                 615                 620

Ser Leu Ser Pro Gly Lys
625                 630
```

(2) INFORMATION FOR SEQ ID NO:7:

(i) SEQUENCE CHARACTERISTICS:
        (A) LENGTH: 442 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:7:

Lys Leu Thr Thr Met Asp Trp Thr Trp Arg Phe Leu Phe Val Val

-continued

```
  1               5                    10                       15
Ala Ala Ala Thr Gly Val Gln Ser Gln Val Gln Leu Val Gln Ser Gly
               20                  25                  30
Ala Glu Val Lys Lys Pro Gly Ser Ser Val Lys Val Ser Cys Lys Ala
               35                  40                  45
Ser Gly Gly Thr Phe Ser Ser Tyr Ala Ile Ser Trp Val Arg Gln Ala
 50                         55                  60
Pro Gly Gln Gly Leu Glu Trp Met Gly Gly Ile Ile Pro Ile Phe Gly
 65                  70                  75                  80
Thr Ala Asn Tyr Ala Gln Lys Phe Gln Gly Arg Val Thr Ile Thr Ala
                    85                  90                  95
Asp Glu Ser Thr Ala Arg Asp Asn Gly Ala Tyr Cys Ser Gly Gly Ser
               100                 105                 110
Cys Tyr Ser Gly Trp Phe Asp Pro Trp Gly Gln Gly Thr Leu Val Thr
               115                 120                 125
Val Ser Ser Ala Ser Thr Lys Gly Pro Ser Val Phe Pro Leu Ala Pro
 130                        135                 140
Ser Ser Lys Ser Thr Ser Gly Gly Thr Ala Ala Leu Gly Cys Leu Val
145                 150                 155                 160
Lys Asp Tyr Phe Pro Glu Pro Val Thr Val Ser Trp Asn Ser Gly Ala
                    165                 170                 175
Leu Thr Ser Gly Val His Thr Phe Pro Ala Val Leu Gln Ser Ser Gly
               180                 185                 190
Leu Tyr Ser Leu Ser Ser Val Val Thr Val Pro Ser Ser Ser Asp Lys
                    195                 200                 205
Lys Val Glu Pro Lys Ser Cys Asp Lys Thr His Thr Cys Pro Pro Cys
 210                        215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                    245                 250                 255
Val Val Val Asp Val Ser His Glu Asp Pro Glu Val Lys Phe Asn Trp
               260                 265                 270
Tyr Val Asp Gly Val Glu Val His Asn Ala Lys Thr Lys Pro Arg Glu
                    275                 280                 285
Glu Gln Tyr Asn Ser Thr Tyr Arg Val Val Ser Val Leu Thr Val Leu
 290                        295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                    325                 330                 335
Gln Pro Arg Glu Pro Gln Val Tyr Thr Leu Pro Pro Ser Arg Asp Glu
               340                 345                 350
Leu Thr Lys Asn Gln Val Ser Leu Thr Cys Leu Val Lys Gly Phe Tyr
                    355                 360                 365
Pro Ser Asp Ile Ala Val Glu Trp Glu Ser Asn Gly Gln Pro Glu Asn
               370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                    405                 410                 415
Val Phe Ser Cys Ser Val Met His Glu Ala Leu His Asn His Tyr Thr
               420                 425                 430
```

-continued

```
Gln Lys Ser Leu Ser Leu Ser Pro Gly Lys
        435                 440

(2) INFORMATION FOR SEQ ID NO:8:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:8:

CGGAATTCCA GTACTACTCA CCTGGTCCGC CGATGGTCTC CGGGC                        45

(2) INFORMATION FOR SEQ ID NO:9:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:9:

CCAGATATAC GCGTTGACAT TGATTATTGA CTAGTTATT                               39
```

US 6,613,746 B1

AGP-ANTIBODY FUSION PROTEINS AND RELATED MOLECULES AND METHODS

This application is a continuation-in-part of Seed et al., U.S. Ser. No. 07/618,314, filed Nov. 23, 1990 now abandoned.

BACKGROUND OF THE INVENTION

This invention relates to AGP-antibody fusion proteins, DNA, and uses thereof.

ELAM-1 is an integral membrane adhesion protein. It possesses an extracellular domain including an N-terminal lectin-related segment, an epidermal growth factor related repeat, and multiple complement regulatory protein motifs (Bevilacqua et al., *Science* 243:1160, 1989; Stoolman et al., *Cell* 56:907, 1989). ELAM-1 is specifically expressed on the surface of endothelial cells activated by the cytokines IL1 and tumor necrosis factor (TNF) (Bevilacqua et al., *Proc. Natl. Acad. Sci. USA* 84:9238, 1987), or the peptide hormone Substance P (Matis et al., *J. Invest. Dermatol.* 94:492, 1990). It mediates adhesion of myeloid cells (e.g., neutrophilic granulocytes) to cytokine-activated endothelial cells (Bevilacqua et al., *Proc. Natl. Acad. Sci USA* 84:9238, 1987). It has been suggested that ELAM-1 is involved in the regulation of inflammatory and immunological events at the interface of the blood and the blood vessel wall (Bevilacqua et al., *Science* 243:1160, 1989).

SUMMARY OF THE INVENTION

In a first aspect, the invention features a method of inhibiting the binding of a cell bearing a cell adhesion protein to a molecule or cell bearing a carbohydrate determinant specific for the cell adhesion molecule. The method involves contacting the cell adhesion protein-bearing cell with an $\alpha_1$-acid glycoprotein (AGP)-antibody fusion protein bearing the carbohydrate determinant.

In a second aspect, the invention features a method of reducing inflammation in a human patient involving administering to the patient a therapeutically-effective amount of an AGP-antibody fusion protein bearing a sialyl-Le$^X$ determinant.

In a third aspect, the invention features an AGP-antibody fusion protein to which there is covalently bonded a carbohydrate determinant specific for a cell adhesion protein.

In related aspects, the invention features purified nucleic acid encoding an AGP-antibody fusion protein containing sites for the attachment of a carbohydrate determinant which is specific for a cell adhesion protein; a vector including such nucleic acid; and a recombinant cell including such a vector.

In preferred embodiments of each of the above aspects, the cell adhesion protein is a selectin, such as ELAM-1; the carbohydrate determinant is sialyl-Le$^X$; the sialyl-Le$^X$ determinant is N-linked or O-linked; the AGP-antibody fusion protein contains multiple sialyl-Le$^X$ determinants; the AGP-antibody fusion protein includes, as an antibody portion, an IgG1 CH2, CH3, or hinge domain; the AGP-antibody fusion protein includes one or more of the N-linked glycan addition sites of $\alpha_1$-acid glycoprotein; the antibody portion of the AGP-antibody fusion protein bears one or more non-naturally occurring carbohydrate determinants; the carbohydrate determinant interferes with the antibody's ability to fix complement and bind an $F_c$ receptor (for example, due to a carbohydrate determinant attached to one or more of amino acids 274, 287, or 322 of the sequence shown in FIG. 1); and the AGP-antibody fusion protein is soluble.

In a final aspect, the invention features a method of protecting a mammal against any adverse immune reaction (including, without limitation, sepsis, organ damage attributable to inappropriate leukocyte extravasation, adult respiratory distress syndrome, glomerular nephritis, and rhumatoid arthritis), the method including administering to the mammal a therapeutically-effective amount of an AGP-antibody fusion protein. Preferably, the method involves treating a mammal for an adverse immune reaction which is induced by a microbial factor. Such microbial factors include, without limitation, gram-negative bacteria lipopolysaccharides (LPS), peptidoglycans from gram-positive organisms, mannan from fungal cell walls, polysaccharides, extracellular enzymes (e.g., streptokinase) and toxins (e.g., toxic shock enterotoxins of staphylococci). In other preferred embodiments, the method involves treating a mammal for any adverse immune reaction (see supra) which is induced by a host factor. Such host factors include, without limitation, metabolites of complement, kinin, and coagulation systems, factors released from stimulated cells (e.g., cytokines such as interleukin 1 (IL1) and tumor necrosis factor-$\alpha$ (TNF)), enzymes and oxidants from polymorphonuclear leukocytes (PMNs), vasopeptides (e.g., histamine), and products of the metabolism of arachidonic acid. In other preferred embodiments, the adverse immune reaction is induced by recombinant TNF-$\alpha$ or is induced by recombinant IL1. In yet other preferred embodiments, the adverse immune reaction is septic shock or is septicemia.

In other preferred embodiments, the AGP-antibody fusion protein bears one or more carbohydrate determinants capable of interfering with the antibody's ability to fix complement and bind an $F_c$ receptor; the antibody portion of the AGP-antibody fusion protein consists of the CH2 and CH3 antibody domains; and the antibody portion of the AGP-antibody fusion protein is an IgG1 domain.

By "cell adhesion protein" is meant a protein, present at some point in its in vivo existence on the cell surface, which mediates a specific interaction with a protein (e.g., a protein bearing a carbohydrate ligand) on the surface of a second cell.

By "carbohydrate determinant" is meant a moiety containing one or more carbohydrate groups which is present on a cell surface (at some point in its in vivo existence) and which interacts in a specific manner with a protein, e.g., a cell adhesion protein, e.g., on the surface of a second cell.

By "selectin" is meant a member of a family of cellular adhesion molecules that are characterized structurally by the presence of a lectin-like domain, an epidermal growth factor-like domain, a series of cysteine-rich repeats, a transmembrane domain and a short cytoplasmic tail.

By "non-naturally occurring" is meant, in this case, any carbohydrate determinant that is not one which is naturally bound to the fusion protein at that amino acid location.

By "inflammation" is meant a pathologic process consisting of cytologic and histologic reactions that occur in the affected blood vessels and adjacent tissues in response to an injury or abnormal stimulation caused by a physical, chemical, or biologic agent.

By "purified nucleic acid" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "N-linked" is meant bonded to the amide nitrogen of an asparagine residue of a protein.

By "O-linked" is meant bonded to the hydroxyl-group oxygen of a serine, threonine, or hydroxylysine residue of a protein.

DESCRIPTION OF THE PREFERRED EMBODIMENTS

The drawings will first briefly be described.

DRAWINGS

FIGS. 1A–1D (SEQ. ID NOS: 1, 2 and 7) shows the sequence of IgG1 and mutations designed to create N-linked glycan addition sites.

FIG. 4 is a graph showing the degree of binding of a series of mammalian cell lines to an ELAM-1-IgG1 fusion protein.

FIGS. 5A–5F is a graph showing the degree of binding of a series of mammalian cell lines to antibodies directed against the cell surface molecules, CD15, CD63, or sialyl-$Le^X$.

Figure 2:
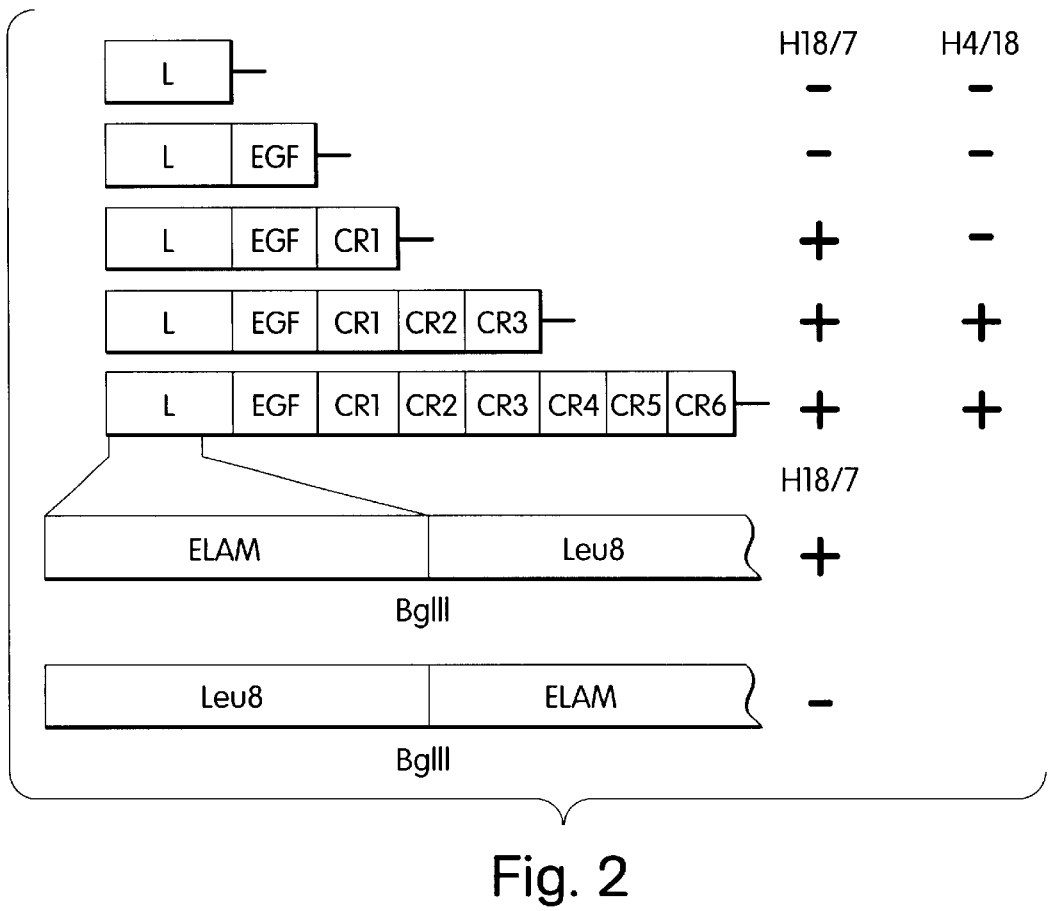
FIG. 2 is a graph showing the binding capability of α-ELAM-1 antibodies to a series of ELAM-1 sub-fragments and ELAM-1 fusion proteins.

FIGS. 15A and 15B is the nucleotide sequence (Panel A; SEQ ID NO: 3) and amino acid sequence (Panel B; SEQ ID NO: 4) of an AGP-IgG1 fusion protein.

FIGS. 16A and 16B is the nucleotide sequence (Panel A; SEQ ID NO: 5) and amino acid sequence (Panel B; SEQ ID NO: 6) of an CD4-IgG1 fusion protein.

Antibody bearing multiple sialyl-$Le^X$ determinants

In one embodiment, the invention features an antibody bearing one or more carbohydrate side chains which mask the CH2 portion of the immunoglobulin molecule and thus inhibit complement fixation and $F_c$ receptor binding. Such antibodies are useful for disrupting undesirable interactions between cells or proteins, or, generally, for disrupting an interaction between any two molecules, one of which bears a determinant specifically recognized by an antibody. Because the carbohydrate moieties block the immunoglobulin domain which triggers complement fixation and $F_c$ receptor binding, such antibodies do not elicit the undesirable side effects (i.e., those resulting from complement fixation and $F_c$ receptor binding) frequently associated with antibody-based therapies. Preferably, the carbohydrate groups serve not only to inhibit undesirable complement fixation and $F_c$ receptor binding, but also perform the function of competitively inhibiting a carbohydrate ligand-cell adhesion protein interaction. Where the carbohydrate groups perform this function, the antibody generally does not serve any function arising from its specificity, but serves only as a carrier for the carbohydrate groups. There is described below such a molecule, in which the carbohydrate side chain includes the sialyl-$Le^X$ determinant. Sialyl-$Le^X$ normally acts to facilitate interaction between cells which bear it (e.g., neutrophils) and cells which bear the protein, ELAM-1 (e.g., endothelial cells, e.g., those lining the blood vessel walls). Disrupting this interaction has therapeutic applications, for example, in minimizing inflammation, such as that which occurs following tissue injury, e.g., myocardial infarction, which is characteristic of diseases such as psoriasis or rheumatoid arthritis, or for preventing or inhibiting septicemia or septic shock which is induced by a microbial- or host-mediated immune reaction.

Because N-linked glycan addition sites are well known to be: N X S/T (where N is asparagine, S is serine, T is threonine, and X is any amino acid except proline), we designed a molecule including several such sites for attachment of sialyl-$Le^X$ side chains. Inspection of the IgG1 sequence (FIG. 1; SEQ. ID NOS: 1 and 7) reveals at least five sites at which N-linked glycan addition sites may be introduced into the molecule in advantageous locations, where complement fixing and $F_c$ receptor binding ability will be impaired by the process These sites (i.e., beginning at amino acid residues 274, 287, 295, 322, and 335), although these are preferred sites of N-linked glycan addition they are not the only candidates; other useful sites may be identified and incorporated into the IgG1 sequence using, as guidance, the following criteria: (1) The sites are, preferably, located in the CH2 region of the immunoglobulin molecule, i.e., in the portion of the molecule responsible for complement fixation and $F_c$ receptor binding; (2) the sites are located in regions of the sequence, predicted by their hydrophilic nature, to be present on the outside of the immunoglobulin molecule and therefore accessible to the enzymes responsible for attachment of carbohydrate side chains; (3) the sites are located in a region which is minimally disruptive to the primary amino acid sequence and, thus, the predicted secondary amino acid structure. For example, a naturally-occurring site which differs from an N-linked glycan addition site by a single amino acid would be preferable to a site requiring two alterations in the amino acid sequence. Moreover, it is preferable to create an N-linked glycan addition site by subsituting amino acids of similar charge or polarity (e.g., substitution of one uncharged amino acid for another). One or more N-linked glycan addition site substitutions may be engineered into the IgG1-encoding sequence; such sequences (i.e., those which encode an antibody molecule to which sialyl-$Le^X$ moieties are attached) are termed IgG1-sialyl-$Le^X$ or IgG1-$Le^X$.

A particular IgG1 molecule bearing sialyl-Le$^X$ moieties is produced as follows. The IgG1 gene is publically available, and its sequence is shown in FIG. 1 (SEQ.ID NO.:1). The gene is mutagenized by standard methods of in vitro site-directed mutagenesis in order to introduce one or more N-linked glycan addition sites (e.g., those described above and shown above the naturally-occurring sequence in FIG. 1; SEQ ID NO:2). The gene is then inserted into a vector designed to express the protein in a eukaryotic cell (see, e.g., those vectors described in Gillies et al., U.S. Pat. No. 4,663,281, hereby incorporated by reference). The eukaryotic host cell is preferably a mammalian cell (e.g., a CHO or lec11 cell), and the expression vector containing the mutated IgG1-Le$^X$-encoding sequence is introduced into the host cell by transient or stable transfection using standard techniques. Such host cells are also transfected (transiently or stably) with a vector capable of expressing an $\alpha(1,3)$ fucosyltransferase capable of attaching the sialyl-Le$^X$ groups to the antibody molecule at the glycosylation sites. The $\alpha(1,3)$fucosyltransferase gene may be expressed from a vector distinct from that encoding IgG1-Le$^X$, or both genes may be carried on, and expressed from, a common vector. Mammalian cells are particularly useful hosts for the synthesis of IgG1-Le$^X$ because they provide all required precursors for sialyl-Le$^X$ production.

An $\alpha(1,3)$fucosyltransferase cDNA is described in Lowe et al. (*Cell* 63:475, 1990). The $\alpha(1,3)$fucosyltransferase enzyme, encoded by this cDNA, recognizes a sialylated precursor molecule and adds either an $\alpha(1,3)$- or an $\alpha(1,4)$-linked fucose moiety to N-acetylglucosamine side chains. The sialyl-Le$^X$ determinant is characterized by an $\alpha(1,3)$-linkage, and, as such, the $\alpha(1,3)$fucosyltransferase enzyme of Lowe (supra) produces both the desired sialyl-Le$^X$-modified molecules and products bearing $\alpha(1,4)$-linked fucose which, although not active in binding to ELAM-1, do not interfere with the action of the sialyl-Le$^X$-modified molecules nor produce other undesirable side effects.

Production of IgG1-sialyl-Le$^X$ would be more efficient, however, if an $\alpha(1,3)$fucosyltransferase was utilized which exclusively catalyzed $\alpha(1,3)$ fucose linkages. Such a mammalian enzyme exists, and the cDNA therefor can be isolated as follows. A cDNA library, prepared from mRNA which is isolated from a myeloid cell line (e.g., HL-60), is inserted into a mammalian cell expression vector such as πH3M (see, Simmons et al., *Nature* 331:624, 1988; Aruffo and Seed, *Proc. Natl. Acad. Sci. USA* 84:8573, 1987) and transfected into a mammalian cell line, preferably, COS7 cells (as described in Seed and Aruffo, *Proc. Natl. Acad. Sci. USA* 84:3365, 1987). The proper cDNA clone is isolated by the immunoselection procedure described in Aruffo and Seed, supra; Seed and Aruffo, supra; and U.S. patent application Ser. No. 07/379,076, hereby incorporated by reference. Transfected cells are harvested and incubated with monoclonal antibodies PM-81 (anti-CD15; Medarex, West Lebanon, N.H.), FMC13 (anti-CD15; Sera-Lab/Accurate Chemical and Scientific, Westbury, N.Y.), MC1 (anti-CD15; Sera-Lab. Westbury, N.Y.) and VIM8 (anti-CD65). Following incubation (e.g., for 1 hour), cells are separated from free antibody by centrifugation through a cushion of 2% Ficoll in PBS and allowed to settle on plastic dishes coated with affinity-purified goat antibodies to mouse IgM (as described below). Adherent cells are collected and a Hirt supernatant containing episomal DNA is prepared. The purified Hirt supernatant DNA is transformed (e.g., by electroporation) into *E. coli* (preferably, *E. coli* MC1061/p3) by standard techniques and ampicillin- and tetracycline-resistant colonies selected by standard methods. Antibiotic resistant colonies are then pooled and the plasmids amplified (e.g., following addition of spectinomycin hydrochloride overnight). The resulting culture is converted to spheroplasts and the spheroplasts fused to COS7 cells by standard procedures (see, for example, Seed and Aruffo, supra). Cells are allowed to incubate (preferably, 2 to 3days) and are exposed to antibodies as described above. Preferably, two rounds of spheroplast fusion and "panning" (i.e., the procedure described above) are performed, and the bacterial cells resulting from the last round of panning are collected, and their plasmid DNA prepared. This cDNA encodes an enzyme, i.e., an $\alpha(1,3)$fucosyltransferase, which directs the appearance of the desired CD15 and CD65 determinants, i.e., the sialyl-Le$^X$ determinant.

Host cells expressing $\alpha(1,3)$fucosyltransferase and IgG1-Le$^X$ (and thus producing an IgG1 molecule bearing sialyl-Le$^X$ determinants) are grown by standard methods and the IgG1-Le$^X$ protein is purified from a cell lysate based on its affinity for a Protein A column or any other standard technique of antibody isolation and purification.

Use

For administering such a compound to a patient, the pharmaceutically-pure IgG1-Le$^X$ is suspended in an acceptable carrier, e.g., physiological saline, and is delivered to patients intravenously in a single or in multiple doses. Optimally, a sufficient quantity of IgG1-Le$^X$ is provided to saturate all ELAM-1-binding sites on an endothelial cell. Typically, this may be achieved with doses of 0.1 mg/kg or greater. The preferred dosage is in the range of 0.1–2.0 mg/kg.

The carrier molecule, for example sialyl-Le$^X$-modified $\alpha_1$-acid glycoprotein-antibody fusion proteins (described below) would be produced generally as described herein and would be administered intravenously to patients as described above (i.e., preferably, at a dose sufficient to saturate all cellular ELAM-1 binding sites, e.g., at 0.1 mg/kg or greater).

IgG1-sialyl-Le$^X$ or sialyl-Le$^X$-modified $a_1$-AGP-antibody fusion proteins may be used, in one example, for the treatment of a patient suffering from a heart attack. Following such a trauma, the endothelial cells lining the blood vessels express ELAM-1 on their surfaces and, without treatment, neutrophils, bearing sialyl-Le$^X$ on their surfaces, bind such ELAM-1-bearing endothelial cells, contributing to inflammation. Treatment with a sialyl-Le$^X$ bearing molecule would attenuate the inflammation by competitively inhibiting the interaction between the invading neutrophils and the blood vessel endothelial cells in the vicinity of the heart. Compounds such as IgG1 sialyl-Le$^X$ or sialyl-Le$^X$-modified $\alpha_1$-AGP-antibody fusions may also be used, as described above, for the treatment of septic shock, septicemia, or any disease characterized by chronic inflammatory conditions, e.g., rheumatoid arthritis, psoriasis, or pemphigus vulgaris. In addition, antibodies or antibody fusion proteins according to the invention may be used in conventional techniques of antibody based therapies or in vivo diagnostics, taking advantage of the antibody's specificity to target therapeutic diagnostic sites. Again, attached carbohydrates determinants mask the CH2 domain of the antibody and block the undesirable effects of complement fixation and $F_c$ receptor binding.

Experimental Information

Sialyl-Lewis X (sialyl-Le$^X$) determinants were shown to interact with ELAM-1 and facilitate binding to ELAM-1 bearing endothelial cells by the following experiments. These examples are presented to illustrate, not limit, the invention.

Recognition by ELAM-1 of the Sialyl-Le$^X$ Determinant

The ELAM-1 domains necessary for granulocyte-binding activity were localized using two monoclonal anti-ELAM-1 antibodies: H18/7, which effectively blocks leukocyte adhesion to activated endothelium, and H4/18, which does not (Pober et al., *J. Immunol.* 136:1680, 1986; Bevilacqua et al., *Proc. Natl. Acad. Sci. USA* 84:9238, 1987). Full length ELAM-1 was expressed from the cDNA carried on plasmid, pELAM-1 (Bevilacqua et al., *Science* 243:1160, 1989). Carboxyl terminal deletions of the ELAM-1 cDNA were created by polymerase chain reaction to produce the proteins shown in FIG. 2. Primer sequences for the PCR deletions were designed based on the full-length ELAM-1 sequence of Bevilacqua et al. (*Science* 243:1160, 1989). Once generated, ELAM-1 cDNA fragments were then fused, by standard techniques, to the transmembrane and intracellular coding portions of a CD7 cDNA (i.e., nucleotides 501 to 1236 of the CD7 cDNA described in Aruffo and Seed, *EMBO. J.* 6:3313, 1987). Plasmids bearing the resulting fusions were transfected into COS cells. Reactivity to monoclonal antibodies was determined by indirect immunofluorescence microscopy of fixed, permeabilized cells by the method of Aruffo et al., *Cell* 61:1303, 1990. The results of this analysis are shown in FIG. 2 and are representative of transfections of three to six independent isolates of the constructs shown. FIG. 2 indicates that H18/7 binding required the lectin-related segment plus the EGF-repeat domains, while H4/18 reactivity required, in addition, the first three complement regulatory protein repeat elements. L indicates the lectin-related segment; EGF indicates the EGF-related repeat segment; and CR1–CR6 indicate complement regulatory protein elements.

To further define the binding site for H18/7, a fragment was exchanged between the ELAM-1 cDNA and the equivalent fragment of the related Leu8 (LECCAM1) cDNA (described in Camerini et al., *Nature* 342:78, 1989). Leu8 (LECCAM-1)/ELAM-1 chimeras were created by restriction fragment interchange from a conserved BglII site within the lectin domain (i.e., at nucleotide 454 and 475 of the ELAM-1 and Leu8 cDNA sequences, respectively). As shown in FIG. 2, H18/7 bound to an antigenic determinant located principally in the first 75% of the ELAM-1 lectin domain. Together with the above result (i.e., that both the lectin-like and EGF-repeat-like domains were required for H18/7 binding to truncated ELAM-1) suggests that the EGF-related repeat element may play a role in shaping the structure of the lectin domain.

Figure 3:
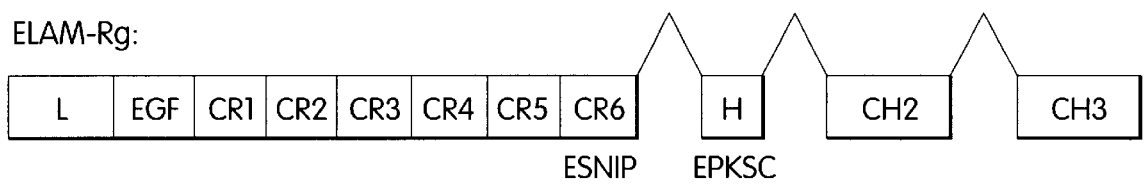
FIG. 3 is a representation of the domain structure of an ELAM-1-IgG1 fusion protein.

To study the possible lectin-carbohydrate interactions suggested by the epitope mapping, a soluble ELAM-1 protein chimera was prepared by the fusion of a cDNA fragment encoding the ELAM-1 extracellular domain to a genomic fragment encoding the hinge, i.e., the CH2 and CH3 domains, of human IgG1 (Aruffo et al., *Cell* 61:1303, 1990; FIG. 3). The ELAM-1-IgG1 chimera was prepared as follows. Synthetic oligonucleotides having the sequence: CGGAATTCCAGTACTACTCACCTGGTC- CGCCGATGGTCTCCGGGC (SEQ. ID NO.: 8) and CCA- GATATACGCGTTGACATTGATTATTGACTAGTTATT (SEQ. ID NO.:9), and corresponding to the splice donor/ carboxyl terminus of ELAM-1 and to a location in the vector upstream of the inserted cDNA, respectively, were prepared by standard techniques. Polymerase chain reaction with these oligonucleotides and the ELAM-1 cDNA expression plasmid, pELAM-1, as template, yielded an 1800 bp fragment which was digested with XhoI and EcoRI and subcloned into XhoI/EcoRI-digested expression vector πH3M (Aruffo and Seed, *Proc. Natl. Acad. Sci. USA* 84:8573, 1987). The subcloned fragment was released by digestion with XhoI and ScaI and ligated to the XhoI/ScaI-digested IgG1 expression plasmid described in Aruffo et al. *Cell* 61:1303, 1990. The resulting construct was transfected into COS cells (as described in Seed and Aruffo, *Proc. Natl. Acad. Sci* 84:3365, 1987), and the desired fusion protein, termed ELAM-Rg, was recovered from the supernatant by adsorption to and elution from protein A-agarose as described in Aruffo et al. (*Cell* 61:1303, 1990). The initial construct, and a subsequent version in which the majority of the PCR-amplified segment (i.e., nucleotides 1 to 1464 of the ELAM-1 sequence) was replaced by a homologous restriction fragment interchange (to avoid potential mutations introduced during amplification) showed identical binding activity. The soluble protein appeared in the form of disulfide-linked dimers, presumably mediated by the hinge region cysteine residues responsible for the inter-heavy chain linkage of active immunoglobulins.

To determine whether myeloid cells bound soluble ELAM-1, plastic dishes precoated with goat-anti-human IgG antibodies, were incubated with supernatants expressing ELAM-Rg. These experiments were carried out as follows. Human granulocytes were isolated from freshly drawn, heparinized whole blood by centrifugation through Ficoll/ sodium diatrizoate (Mono-Poly Resolving Medium, Flow Laboratories, McLean, Va.) for 20 min. at 800×g. Cell lines were obtained from the American Type Culture Collection (ATCC) and were maintained in IMDM with 10% fetal bovine serum as described in Aruffo and Seed (*Proc. Natl. Acad. Sci. USA* 84:8573, 1987). Adhesion to ELAM-Rg was carried out in bacterial culture dishes (Falcon 1008, Becton-Dickinson Labware, Lincoln Park, N.J.) to which affinity-purified goat anti-human IgG antibody (Organon Teknika/ Cappel, Malverne Pa.) had been allowed to adsorb at 10 μg/ml in 50 mM Tris-HCl, pH 9.5 for at least one hour. Remaining protein binding sites were then blocked by overnight incubation with 1 mg/ml bovine serum albumin in Phosphate Buffered Saline (PBS; 137 mM NaCl, 2.7 mM KCl, 4.3 mM $Na_2HPO_4.7H_2O$, 1.4 mM $KH_2PO_4$, pH7.3). Dishes were incubated with ELAM-Rg (≈1 μg/ml) for 30 min. at 22°, washed with PBS, overlaid with cells ($10^6$ cells) for 10 min. at 22°, and washed three times with PBS. The adherent cells per unit area of dish were enumerated with the aid of an ocular reticle and scored as follows: >100 cells, +++++; 100–75 cells, ++++; 75–50 cells, +++; 50–25 cells, ++; and 25–10 cells, +. All values represented the average of triplicate determinations.

The treated plastic acquired the ability to specifically bind granulocytes as well as the myeloid cell lines HL60 and THP1 (FIG. 4). Other cell lines of both hematopoietic origin (i.e., U937 and HSB-2) and nonhematopoietic origin (i.e., WIDR) were found to bind to the ELAM-1 coated plastic as well (FIG. 4). Dishes coated with CD8 fusion protein (Aruffo et al., *Cell* 61:1303, 1990) showed negligible affinity (for granulocytes or any of the cell lines tested (Bevilacqua et al., *Proc. Natl. Acad. Sci. USA* 84:9238, 1987).

To correlate the binding activity with surface phenotype, various monoclonal antibodies recognizing known granulocyte carbohydrate antigens were screened for reactivity with the above cell types. $5×10^5$ cells were incubated with the following antibodies (as ascites at 1:250 dilution, or as purified antibody at 4 μg/ml): PM-81 (anti-CD15; Medarex, W. Lebanon, N H; Ball et al., *J. Immunol.* 130:2937, 1983), CSLEX1 (anti-sialyl-Le$^X$; Fukushima et al., *Cancer Res.* 44:5279, 1984); or VIM2 (anti-CD65; Macher et al., *J. Biol. Chem.* 263:10186, 1988), followed by a fluorescein-conjugated goat anti-mouse IgG+IgA+IgM antibody (Organon Teknika/Cappel, Malverne, Pa.).

Results are shown in FIG. 5. Sparse dots represent the negative control (no primary antibody); dense dots, anti-CD15 mAb; solid line, anti-CD63 mAb; and broken line, anti-sialyl-Le$^X$ mAb. The U937 line used herein lacked sialyl-Le$^X$ determinants, unlike the related U937 cell line tested by Terasaki and coworkers (Fukushima et al., *Cancer Res.* 44:5279, 1984). An initial survey showed that ELAM-1 adhesion potential correlated with the presence of the CD15 determinant (i.e., Le$^X$, or lacto-N-fucopentaose III; Gooi et al., *Nature* 292:156, 1981; Huang et al., *Blood* 61:1020, 1983; Magnan et al., *Arch. Biochem. Biophys.* 233;501, 1984; Gooi et al., *Eur. J. Immunol.* 13:306, 1983; Tetteroo et al., *Eur. J. Immunol.* 14:1089, 1984), but not with the determinants associated with CD17 (lactosyl ceramide; Symington et al., *J. Biol. Chem.* 259:6008, 1984), CD65 (VI$^3$NeuAcIII$^3$FucnorLcnOse$_6$Cer; Macher et al., *J. Biol. Chem.* 263:10186, 1988) or sulfatides (Fredman et al., *Biochem. J.* 251:17, 1988).

To further test the correlation between ELAM-1 adhesion potential and the presence of CD15, cells bearing CD15 were treated with neuraminidase, an enzyme known to cleave terminal sialyl groups. HL60 cells ($10^6$/plate) were incubated in 50 μl of 0.15M NaCl, 4 mM CaCl$_2$, pH 5.5, for 1 hr. at 37° in the presence or absence of 41.5 mU of neuraminidase (from Vibrio cholerae, type II, Sigma, St. Louis, Mo.). Cells were washed three times with PBS and adherence to either ELAM-Rg- or PM-81-coated dishes was scored as described above. Dishes were coated with ELAM-Rg as described above, and with purified PM-81 antibody at 10 μg/ml in 50 mM Tris-HCl pH 9.5. Adherence assays were carried out as described above. Results shown in FIG. 6 are expressed as percent of control and were calculated from the mean±standard deviation for the average of triplicate determinations in three independent experiments.

Figure 6:
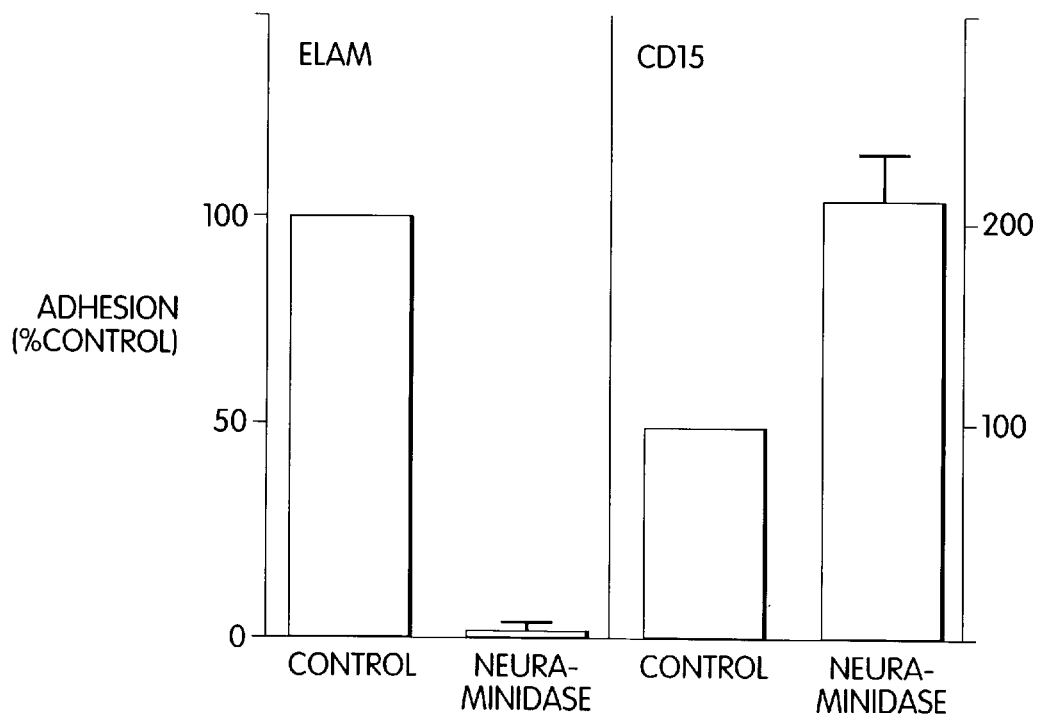
FIG. 6 is a graph showing binding of neuraminidase-treated myeloid cells to ELAM-1 or to α-CD15 antibody.

FIG. 6 indicates that the correlation of ELAM-1 adhesion potential with the presence of CD15 was imperfect because digestion of the cells with neuraminidase abolished binding to ELAM-1 but increased binding to immobilized anti-CD15 antibodies.

Association with CD15 and sensitivity to neuraminidase suggested that the sialylated form of the CD15 carbohydrate antigen might represent the physiological ELAM-1 ligand. To test this idea, CSLEX1 monoclonal antibody was assayed for its ability to inhibit adhesion of HL60 cells to ELAM-Rg. $10^6$ HL60 cells were incubated with CSLEX1 (1:50 in PBS) for 30 min. on ice, then crosslinked with affinity purified goat anti-mouse IgM antibody (Organon Teknika/Cappel, Malverne, Pa.) at 20 μg/ml in PBS for 30 min., and fixed with 2% formaldehyde in PBS for 20 min. at 22°. Cells were washed three times in PBS/1% glycine and incubated with ELAM-1-Rg-coated dishes as described above. The data (presented as percent of control) in FIG. 7 represents the mean±standard deviation of triplicate determinations in three independent experiments.

Figure 7:
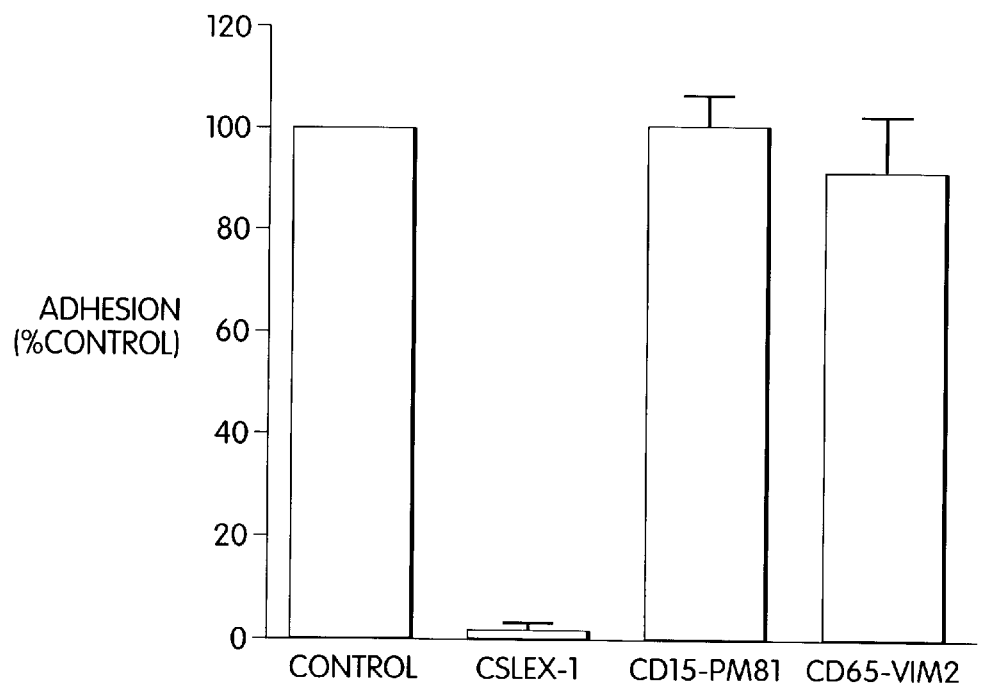
FIG. 7 is a graph showing inhibition of ELAM-1 bearing cell adhesion by α-sialyl-$Le^X$ antibody.

FIG. 7 indicates that there exists a very good correspondence between the surface density of sialyl-Le$^X$ and the rank order of the number of cells bound per unit area of ELAM-Rg coated plastic. In addition, anti-sialyl-Le$^X$ antibody completely inhibited adhesion of myeloid cells to ELAM-1, whereas anti-CD65 and anti-CD15 antibodies had no activity under identical conditions.

The carbohydrate epitope recognized by the CSLEX1 antibody has been reported to be NeuNAcα2-3Galβ1-4 (Fucα1-3)GlcNAcβ1-3Gal, based on motifs common to structurally characterized glycolipids with which the antibody reacts (Fukushima et al., *Cancer Res.* 44:5279, 1984). Chemical analysis of the fucosylated lactosaminoglycans of neutrophilic granulocytes has shown that both the Le$^X$ (CD15) and sialyl-Le$^X$ determinants are predominantly represented on tetraantennary asparagine-linked glycans whose individual strands are built up from poly(N-acetyllactosamine) chains bearing variable α(1,3)-linked fucose substitutions (Fukuda et al., *J. Biol. Chem.* 259:10925, 1984; Spooncer et al., *J. Biol. Chem.* 259:4792, 1984). Serological evidence supports the existence of the sialyl dimeric Le$^X$ determinant on granulocytes as well (Fukushi et al., *J. Biol. Chem.* 259:10511, 1984; Fukushi et al., *Cancer Res.* 45:3711, 1985). As such, the residue on the reducing side of the sialyl-Le$^X$ group is galactose in all of the granulocyte structures thus far identified. Although antibody CSLEX1 blocks binding, the structure recognized by ELAM-1 might be more complex than the structure recognized by CSLEX1. To establish the minimum glycan structure for ELAM-1 binding, chemically-characterized glycans bearing sialyl-Le$^X$ determinants were evaluated for ELAM-1 recognition.

Amniotic fluid is one source of well defined sialyl-Le$^X$ determinant which is found in a very different context than the granulocyte cell surface. The sialyl-Le$^X$-bearing carbohydrate of amniotic mucins is joined β1-6 to a 3-substituted N-acetylgalactosamine, which in turn is attached directly to the polypeptide backbone through O-linkage to serine or threonine (Hanisch et al., *Carbohydr. Res.* 178:29, 1988). Amniotic fluid-derived sialyl-Le$^X$ determinants were tested for their ability to block binding of myeloid cells to immobilized ELAM-1. Human amniotic fluid (HAF) was either used without purification, fractionated by centrifugal ultrafiltration (100 kDal nominal cutoff; Centricon 100, Amicon, Danvers Mass.), or fractionated, following phenol extraction, by size exclusion chromatography (Sephacryl S-300 HR) in 4M guanidinium chloride (by the method of Hanisch et al., *Carbohydr. Res.* 178:29, 1988) to yield purified mucins. Such mucins were used at a protein concentration of approximately 150 μg/ml. Binding to ELAM-Rg coated plastic was performed as described above. Results (expressed as percent of control) shown in FIG. 8 are the average of triplicate determinations in two independent experiments.

Figure 8:
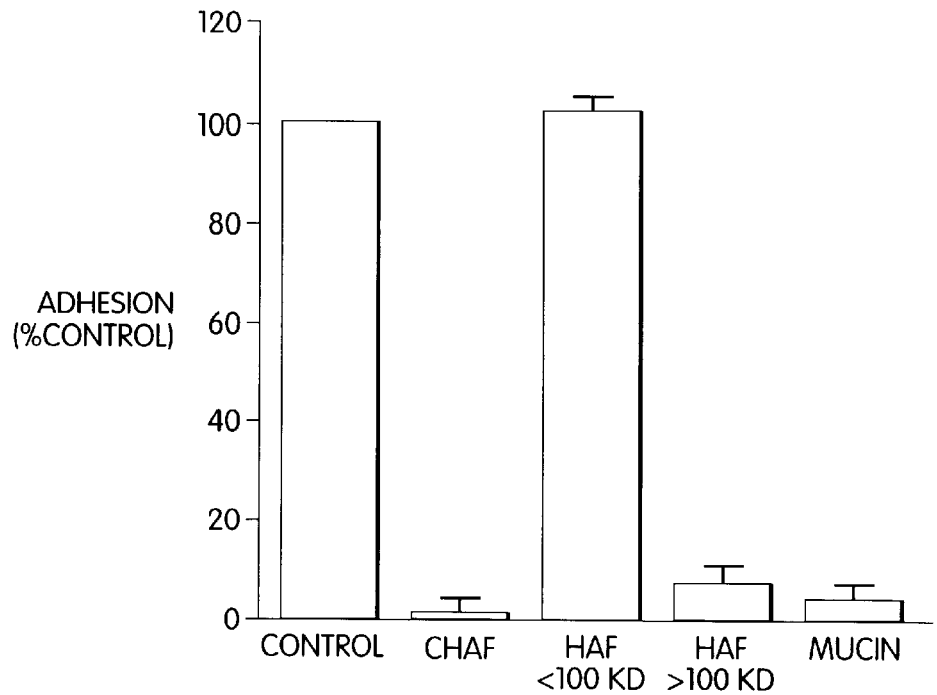
FIG. 8 is a graph showing the effect of amniotic fluid-derived sialyl-$Le^X$ determinant on binding of myeloid cells to ELAM-1.

FIG. 8 indicates that, despite the dissimilarity between the granulocyte glycans and the amniotic fluid mucins, purified amniotic fluid mucins, as well as unfractionated amniotic fluid (which appears to contain all of its activity in the mucin-rich high molecular weight fraction), efficiently blocked binding of myeloid cells to immobilized ELAM-1.

Another source of sialyl-Le$^X$ determinants is fucosylated α$_1$-acid glycoprotein (α$_1$-AGP) (Biou et al., *Biochim. Biophys. Acta.* 913:308, 1987; Wieruszeski et al., *FEBS Lett.* 238:390, 1988). Chemical analysis of human α$_1$-AGP has shown that fucose is present on a minor fraction of N-linked glycans (Schmid et al., *Biochim. Biophys. Acta.* 492:291, 1977; Fournet et al., *Biochemistry* 17:5206, 1978), but that the asialo protein at least partially blocks the binding of anti-CD15 antibodies (Gooi et al., *Eur. J. Immunol.* 13:306, 1983; Tetteroo et al., *Eur. J. Immunol.* 14:1089, 1984). A modest (35±9%) reduction in binding of HL60 cells to ELAM-1 (adsorbed to plastic) was achieved with 200 μg/ml of the protein.

In vitro Production of a Sialyl-Le$^X$ Molecule

To extend these results, enzymatically-fucosylated α$_1$-AGP was prepared in vitro. The biosynthesis of the sialyl-Le$^X$ determinant is controlled by a specific α(1,3) fucosyltransferase (Campbell et al., *Cell* 35:303, 1983; Campbell et al., *J. Biol. Chem.* 259:11208, 1984), which adds fucose to the N-acetylglucosamine moiety of terminal N-acetyllactosamine or its 3-sialyl adduct; a genetically and biochemically distinct specific α(1,3)fucosyltransferase is known to only add fucose to the asialyl precursor (Prieels et al., *Eur. J. Biochem.* 130:347, 1983; Muramatsu et al., *Eur. J. Biochem.* 157:71, 1986). A third fucosyltransferase is known to form both α(1,3) and a α(1,4) linkages, apparently to unsialylated substrates (Prieels et al., *J. Biol. Chem.* 256:10456, 1981; Lowe et al., infra). Biosynthesis of the sialyl-Le$^X$ determinant proceeds by sequential sialylation followed by fucosylation because α(2,3)sialytransferase cannot recognize the fucosylated terminal N-acetyllactosamine that is CD15 (Holmes et al., *J. Biol. Chem.* 261:3737, 1986). α$_1$-acid glycoprotein is a good substrate for the α(1,3)fucosyltransferase of amniotic fluid (e.g., Hanisch et al., *Carbohydr. Res.* 178:23, 1988), an enzyme which forms sialyl-Le$^X$ from sialylated and nonsialylated precursors, respectively.

Amniotic fluid fucosyltransferase was isolated by affinity chromatography and evaluated for its ability to convert α$_1$-AGP into an ELAM-1 ligand as follows. α(1,3) fucosyltransferase was isolated from concentrated amniotic fluid by fetuin-agarose chromatography as previously described in Hanisch et al. (*Carbohydr. Res.* 178:23, 1988) and Mitsakos et al. (*Biol. Chem. Hoppe-Seyler* 369:661, 1988). 0.8 μCi GDP$^{14}$C-fucose (225 Ci/mole) and 100 μg of bovine α$_1$-AGP (Sigma, St. Louis, Mo.) were added to a reaction mix containing 25 mM Tris-HCl pH 7.0, 35 mM MgCl$_2$ and 1 mM ATP in a final volume of 120 μl. The reaction was allowed to proceed for 24 h. at 37°, at which time approximately 10% of the $^{14}$C-labeled fucose had been incorporated into TCA-insoluble material. Unincorporated label was removed by centrifugal ultrafiltration (Centricon 10, Amicon, Danvers, Mass.). 20 μl of a 1:5 dilution of the labelled material, or 10 μl of a 1:5 dilution of a similarly constituted reaction mixture lacking labelled GDP-fucose, was adsorbed to plastic dishes (as described above) or to 96 well microtiter plates (Falcon 3911, Becton Dickinson, Oxnard, Calif.). Wells were incubated at 220 with ELAM-Rg or CD8-Rg at 1 μg/ml for 1 hr., washed with PBS, and incubated with a radioiodinated goat anti-human IgG antibody (DuPont/NEN, Boston, Mass.) for an additional hr. Following washing, labelled antibody binding was measured in a gamma counter. Results shown in FIG. 9 are expressed as the mean±standard deviation of quadruplicate determinations and are representative of two independent experiments.

Figure 9:
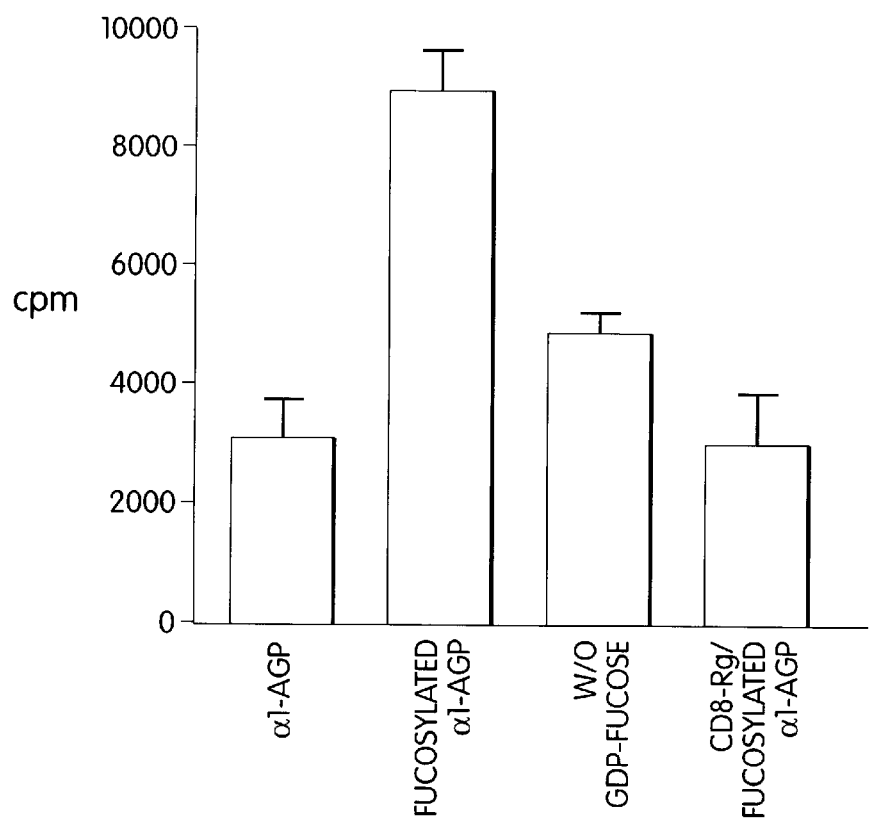
FIG. 9 is a graph showing the ability of in vitro-fucosylated $α_1$-acid glycoprotein to bind ELAM-1.

FIG. 9 shows that α$_1$-AGP incubated with fucosyltransferase in the presence of GDP-fucose bound significantly more ELAM-Rg than did α$_1$-AGP alone, or α$_1$-AGP incubated with enzyme in the absence of GDP-fucose.

The fucosylated glycans of asialo-α-AGP bear the terminal structure Galβ(1-4)-(Fucα(1-3))GlcNAcβ(1-4)Man, while the nonfucosylated termini of the asialoprotein consist of the N-acetyllactosamine group joined either β(1-4), β(1-2), or α(1-6) to mannose (Fournet et al., *Biochemistry* 17:5206, 1978). Hence neither any pre-existing sialyl-Le$^X$ determinants of α$_1$-AGP nor any of the potential fucosyl adducts to N-acetylglucosamine can be joined to galactose. These results, together with the inhibition of ELAM-1 binding by mucin O-linked glycans, indicate that the sialyl-Le$^X$ grouping by itself has appreciable affinity for ELAM-1. It remains to be determined, though, whether quantitatively stronger ELAM-1 binding might be promoted by residues neighboring the sialyl-Le$^X$ determinants on granulocytes or by steric factors affecting their accessibility.

IL-8 Blocks Myeloid Cell Adhesion to ELAM-1

It has been reported that the release of IL-8 from IL-1-treated endothelial cells causes granulocytes to lose the ability to bind to IL1 induced endothelium (Gimbrone et al., *Science* 246:1601, 1989). The effect of IL1 and IL-8 on sialyl-Le$^X$ surface antigen expression was determined as follows. Granulocytes were incubated with IL1β (10 ng/ml; Pepro Tech, Rock Hill, N.J.) or IL-8 (25 ng/ml; Pepro Tech, Rock Hill, N.J.) for 20 min. at 37°, washed three times, and incubated with a monoclonal antibody to either CD15 (PM-81), CD65 (VIM2) or sialyl-Le$^X$ (CSLEX1) (described above) on ice. Results in FIG. 10 are given as the relative mean fluorescence intensity (MFI) determined by flow cytometry, as a percent of the MFI of granulocytes incubated in parallel without cytokines, and are representative of four experiments.

Figure 10:
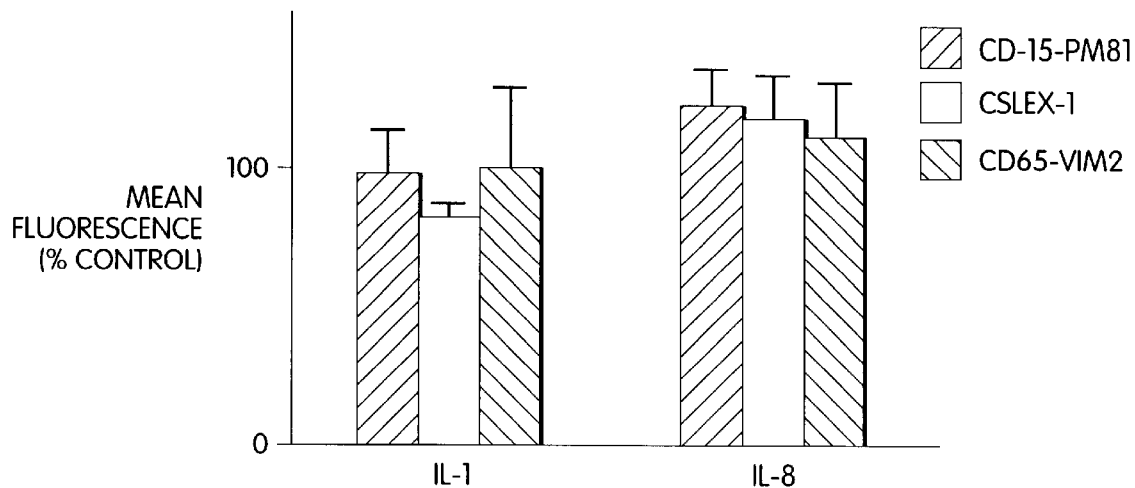
FIG. 10 is a graph showing the effect of IL1 and IL-8 on cell surface expression of sialyl-$Le^X$.

FIG. 10 shows that neither IL1 nor IL-8 caused a substantial reduction in the expression of cell surface sialyl-Le$^X$.

Figure 11:
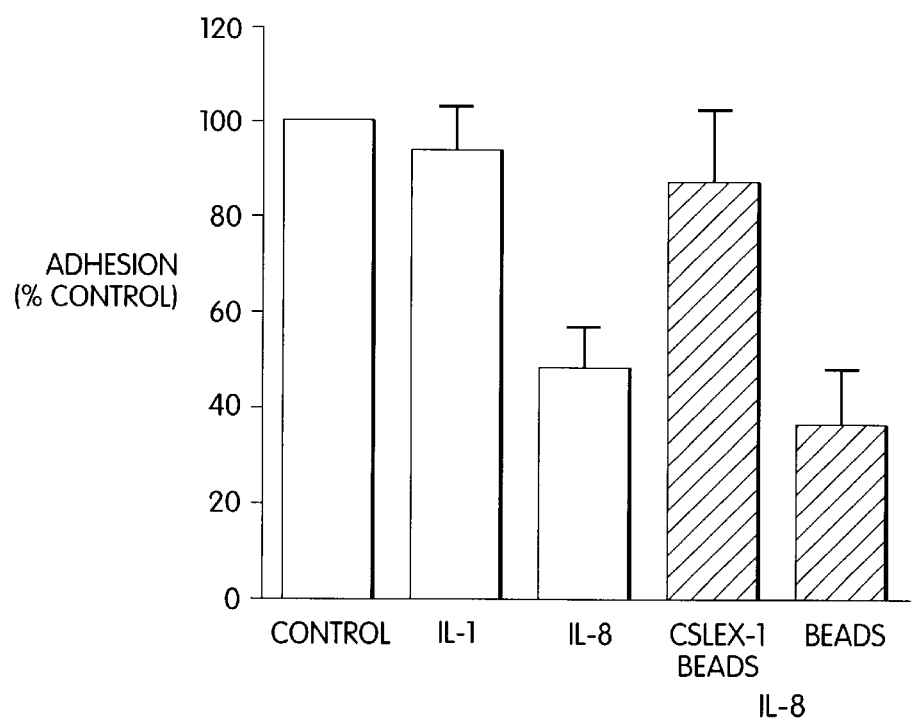
FIG. 11 is a graph showing the effect of IL1 and IL-8 on the adhesion of myeloid cells to ELAM-1.
Figure 12:
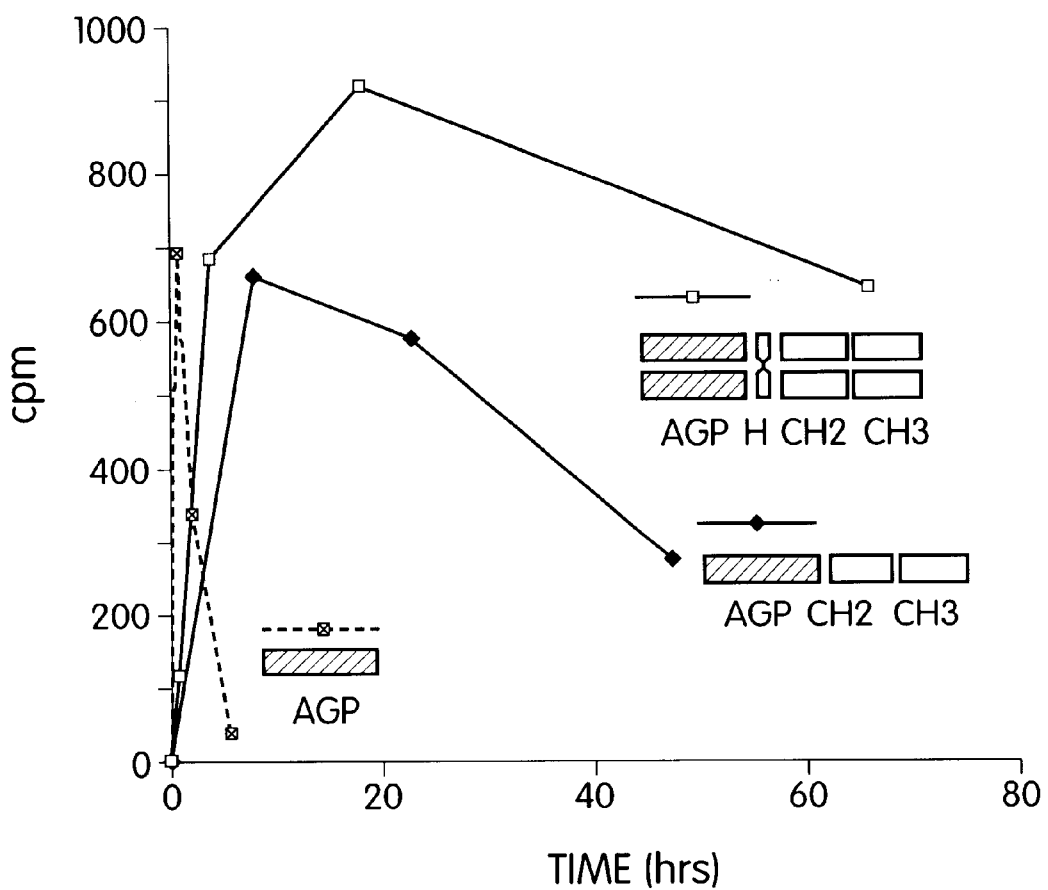
FIG. 12 is a graph showing the plasma half-life of AGP (dotted line), AGP fused to the CH2 and CH3 domains of human IgG1 (solid line, solid triangles), and AGP fused to the hinge, CH2, and CH3 domains of human IgG1 (solid line, open squares).
Figure 13:
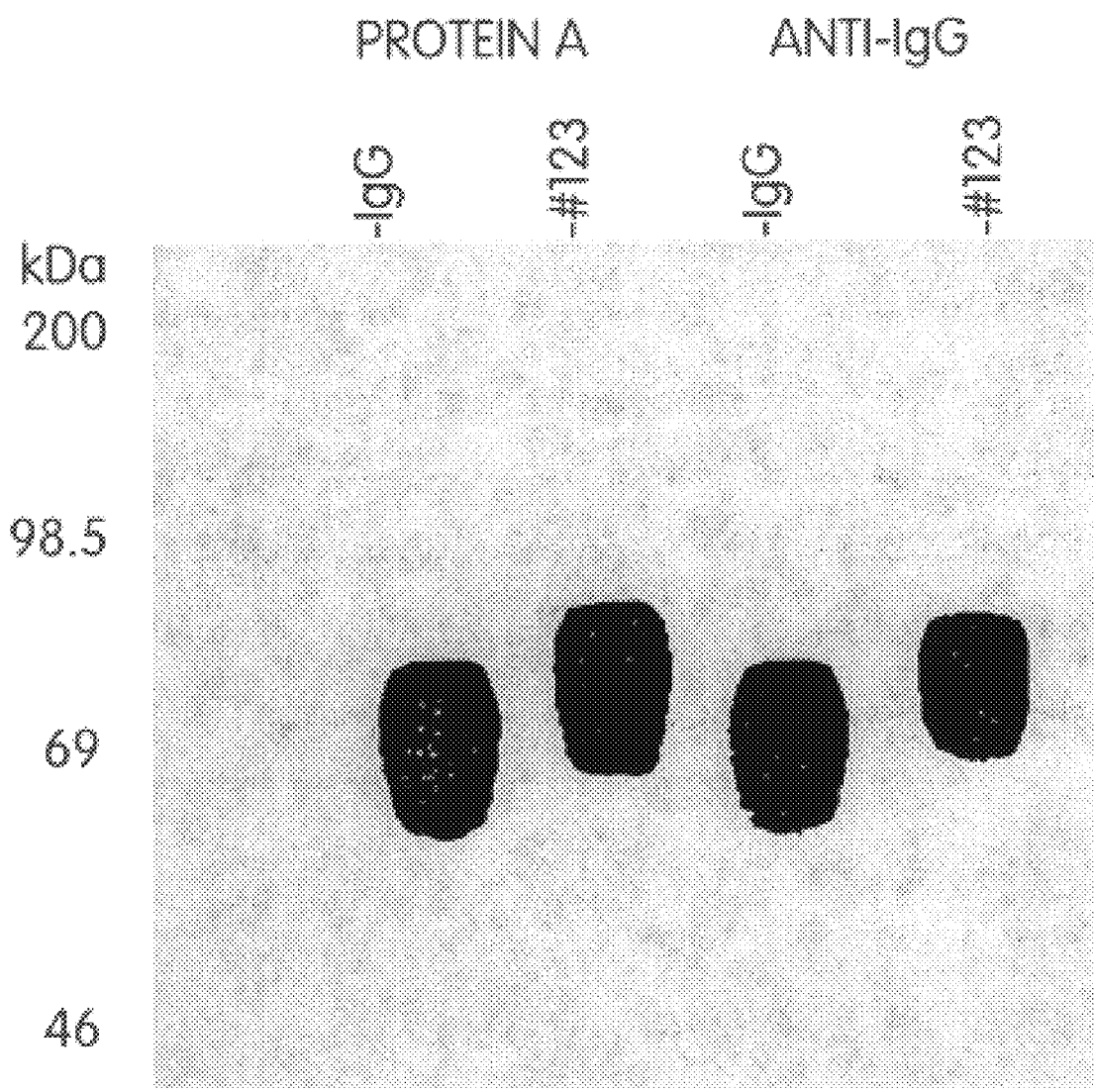
FIG. 13 is a protein gel showing an increase in molecular weight of immunoglobulin fusion proteins upon introduction of additional glycosylation sites into the CH2 domain of human IgG1.
Figure 14:
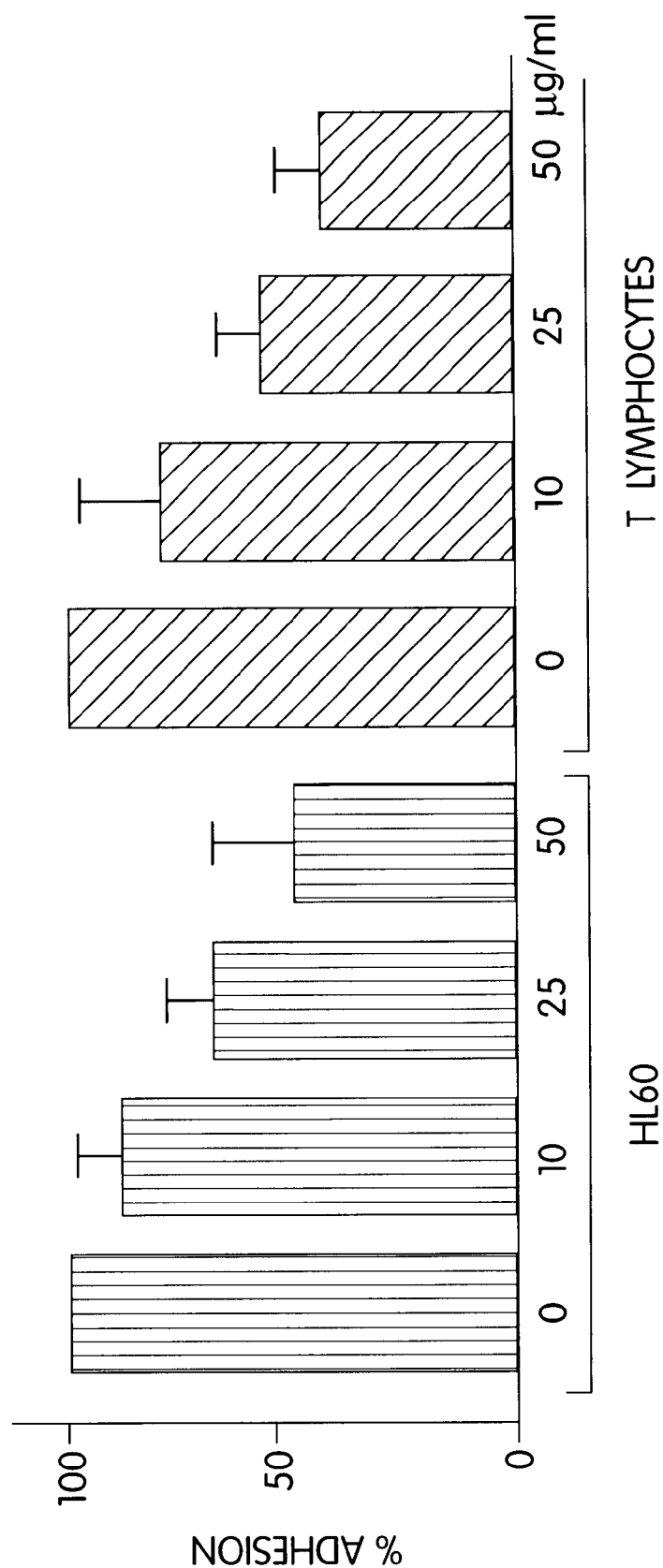
FIG. 14 is a bar graph showing inhibition of adhesion of HL-60 cells and T-lymphocytes to ELAM-1 by an AGP-IgG1 fusion protein.

To test the ability of supernatants harvested from granulocytes exposed to IL-8 to block binding to ELAM-1, granulocytes (5×10$^7$/ml) were incubated with IL1 or IL-8 (at the concentrations above) for 1 hr. at 37°. Supernatants were collected after centrifugation and incubated with ELAM-Rg-coated dishes. Cells were added after 30 min., and binding was determined as described above. Immunoadsorption was performed with 40 μl of Protein-A agarose beads (Sigma, St. Louis, Mo.) to which 10 μg of affinity purified rabbit anti-mouse IgM were adsorbed, followed by 5 μl of CSLEX1 ascites. Control beads were similarly prepared but were not incubated with CSLEX1. The beads were washed with PBS and incubated with the supernatants for 1 hr. at 4°. Results are shown in FIG. 11 and are expressed as the percent of cells bound, relative to the number bound in the presence of supernatants of granulocytes incubated without cytokine under the same conditions. Data shown are mean±standard deviation of triplicate determinations in three independent experiments.

FIG. 11 shows that supernatants harvested from cultures of granulocytes treated with IL-8, but not IL1, blocked the adhesion of HL60 cells to immobilized ELAM-1, and the binding inhibition could be specifically reversed by adsorption of the supernatants with solid-phase CSLEX1, but not with the immunoadsorption matrix alone.

α$_1$-Acid Glycoprotein-Immunoglobulin Fusion Proteins

As discussed herein, antibody fusion proteins according to the invention have important therapeutic and diagnostic uses. Previous work has demonstrated that large amounts of antibody fusion proteins may be generated and secreted transiently from transfected mammalian cells (for example, COS cells). In general, to produce an antibody fusion protein, cDNA encoding a domain of interest is fused in-frame to human IgG domains (for example, constant domains) by standard techniques, and the fusion protein is expressed. The antibody portion of the molecule facilitates fusion protein purification and also prolongs the plasma half-life of otherwise short-lived polypeptides or polypeptide domains. Preferably, antibody fusion proteins are expressed according to the methods disclosed in Seed et al., U.S. Ser. No. 08/483,151 entitled "Fucosyltransferase Genes and Uses Thereof," filed Jun. 7, 1995 (which is hereby incorporated by reference), e.g., using IgG or IgM antibodies or portions thereof.

Recombinant plasmids expressing particular α$_1$-AGP-antibody fusion proteins (e.g., α$_1$-AGP-Hinge-CH2-CH3 and α$_1$-AGP-CH2-CH3 proteins) were constructed as follows. A cDNA encoding the acute phase α$_1$-AGP gene was cloned from a human liver cDNA library by polymerase chain reaction (PCR) using oligonucleotide primers corresponding to the 5' and 3' coding regions of α$_1$-AGP (Board et al., *Gene* 44:127, 1986) according to standard techniques.

The 5' $\alpha_1$-AGP primer was designed to contain a HindIII restriction site and the 3' primer was designed to contain a BamHI restriction site rather than the $\alpha_1$-AGP stop codon. The PCR-amplified product was then digested with HindIII/BamHI and cloned into a HindIII/BamHI-cut plasmid expression cassette (see Aruffo et al., *Cell* 61:1303, 1990) containing constant domains of human IgG1 (i.e., Hinge-CH2-CH3 or CH2-CH3). A nucleotide sequence and amino acid sequence of this AGP-IgG fusion protein is shown in FIGS. 15A and 15B respectively. Resulting expression plasmids were transfected into COS cells (as described in Seed and Aruffo, *Proc. Natl. Acad. Sci* 84:3365, 1987) for the production of soluble $\alpha_1$-AGP antibody fusion proteins or $\alpha_1$-AGP.

To prepare an $\alpha_1$-AGP-IgG1 fusion protein capable of inhibiting complement fixation and $F_c$ receptor binding, we introduced additional sialyl-Le$^x$ consensus glycosylation sites (N-X-T/S) into the CH2 domain of human IgG1 as follows. Three sialyl-Le$^x$ sites were added to the CH2 domain by creating novel glycosylation consensus sites as described supra; the CH2 domain of human IgG1 naturally contains a single glycosylation site. In particular, consensus N-linked glycosylation sites were introduced at amino acid positions #274, #287, and #322 (FIG. 1; SEQ ID NO:2) by mutating amino acids K to N, A to N, and K to N, respectively, using standard methods of in vitro site-directed oligonucleotide mutagenesis (see, Ausubel et al., *Current Protocols In Molecular Biology*, Wiley Interscience, 1995). To maximize base pair substitution, a method based on uracil N-glycosidase repair was used to incorporate the degenerate oligonucleotides into the expression vector. The single-stranded DNA produced by this method contained deoxyuracil residues which allowed for efficient selection of mutated strands. Introduced muations were verified by DNA sequence analysis.

To prepare soluble fusion proteins, expression plasmids were transfected into COS cells stably expressing α(1,3/1,4) fucosyltransferase, and the expressed $\alpha_1$-AGP-IgG1 fusion proteins were isolated as follows. COS cells were incubated with plasmids carrying a fused $\alpha_1$-AGP-IgG1 fusion gene ($\alpha_1$-AGP-Hinge-CH2-CH3 or $\alpha_1$-AGP-CH2-CH3) in medium containing 10% NuSerum (Collaborative Research), DEAE-dextran, and chloroquine diphosphate. After incubation the culture medium was removed, and the cells were briefly exposed to 10% dimethyl sulfoxide (DMSO) in phosphate-buffered saline (PBS). The cells were then transferred to fresh medium containing 10% NuSerum (Collaborative Research), DEAE-dextran, and chloroquine diphosphate. After 7 to 10 days, the culture supernatant was harvested, and soluble $\alpha_1$-AGP-IgG1 fusion protein was purified from the supernatant based on its affinity for protein A agarose beads. The $\alpha_1$-AGP-IgG1 fusion protein was recovered from protein A beads by eluting with dilute acetic acid. Eluate fractions containing $\alpha_1$-AGP-IgG1 fusion protein were neutralized, and then concentrated by centrifugal ultrafiltration. Purified $\alpha_1$-AGP-IgG1 fusion protein was quantified by ELISA using mouse anti-human IgG antisera according to standard methods.

To prepare [$^{35}$S]-radiolabelled recombinant $\alpha_1$-AGP and $\alpha_1$-AGP-IgG1 fusion proteins, the above-described procedure was modified as follows. Twelve hours following transfection, a fraction of the COS cells transfected with each construct were seeded into flasks containing fresh culture medium. Thirty-six hours post-transfection, the cells were then washed with PBS and overlayed with cysteine-methionine-free culture medium for 30 minutes. Next, [$^{35}$S] cysteine and [$^{35}$S] methionine were added to a final concentration of 150 μCi/ml, and the cells were allowed to incorporate label overnight. After labeling, the culture supernatants were harvested and incubated with protein A beads. The protein A beads were collected by centrifugation and washed. Radiolabelled fusion protein was subsequently eluted from the beads using dilute SDS (sodium dodecyl sulfate). For visual analysis, the eluate was electrophoretically separated on a 6% discontinuous polyacrylamide gel with or without prior exposure to mercaptoethanol.

To assess the effect that the fusion of acute phase protein $\alpha_1$-AGP to the 5' end of the human IgG1 (Hinge-CH2-CH3 or CH2-CH3) has on $\alpha_1$-AGP's half-life, we examined the in vivo half-life of recombinant fusion proteins in Balb/c mice. These experiments were carried out as follows. After injecting the mice with radiolabelled [$^{35}$S] $\alpha_1$-AGP-IgG1 fusion proteins or [$^{35}$S] $\alpha_1$-AGP, retroocular blood aliquots were obtained at various time intervals to determine their plasma half-life. Radioactivity of each blood sample was determined in triplicate by standard scintillation spectrometry. As shown in FIG. 12, $\alpha_1$-AGP unfused to IgG1 had a plasma half-life of less than 90 minutes, and was rapidly cleared from the circulation. By contrast, fusion of $\alpha_1$-AGP to either the CH2-CH3 domains (resulting in a monomeric protein) or to the Hinge-CH2-CH3 domains (resulting in a dimeric protein) significantly prolonged the plasma half-life of these recombinant molecules to several days. These results demonstrated the enhanced stability of $\alpha_1$-AGP when fused to IgG1 constant domains such as CH2-CH3 or Hinge-CH2-CH3.

To determine whether the engineered consensus N-linked glycosylation sites were glycosylated in vivo, we examined the molecular weight of recombinant $\alpha_1$-AGP-IgG1 fusion protein produced in COS cells stably expressing α(1,3/1,4) fucosyltransferase. As shown in FIG. 13, expression of fusion protein in COS cells followed by immunoprecipitation with polyclonal sera against anti-human IgG by standard methods revealed an increase in the molecular weight of the mutated IgG1 (termed #123 in FIG. 13) in comparison to an identical fusion protein lacking the three additional sialyl-$Le^X$ sites (termed IgG in FIG. 13), indicating that the additional glycosylation sites were efficiently utilized. In addition, this hyperglycosylated form of $\alpha_1$-AGP-IgG1 retained its affinity for protein A as documented by protein A immunoprecipitation (FIG. 13, Protein A panel).

To test for the ability of the $\alpha_1$-AGP-IgG1 fusion protein (i.e., $\alpha_1$-AGP-Hinge-CH2-CH3) produced in COS cells to inhibit adhesion of human T lymphocytes and myeloid HL60 cells to ELAM-1 (i.e., the adhesion molecule that binds sialyl-$Le^X$), we analyzed the adhesion of human T lymphocytes and myeloid HL60 cells to immobilized ELAM-1 in the presence of increasing concentrations of fusion protein. These experiments were carried out generally as described above. As shown in FIG. 14, at approximately 50 μg/ml of fusion protein, there was a >50% inhibition of adhesion for both cell types (compare 0 μg/ml to 50 μg/ml for both HL60 and T lymphocytes shown in FIG. 14). By contrast, we observed that purified sialyl-$Le^X$ had no effect on adhesion at concentrations up to 200 μg/ml.

Coexpression of the native constant domain of human IgG1 with fucosyltransferase did not result in a molecule capable of binding to ELAM-1.

The introduction of the above-described additional glycosylation sites within the CH2 domain created a molecule that was unrecognized by $F_c$ receptor or complement using assays that are standard in the art; exemplary complement fixation assays include Weir et al., *Handbook of Experimental Immunology*; and Coligan et al. *Current Protocols In*

*Immunology*, Wiley Interscience, 1995. This experiment was conducted using an antibody fusion protein hat contained a CD23 domain joined to an antibody portion hat included the sialyl-Le$^X$ addition sites described above. Because the constant region of the expressed antibody fusion protein protrudes from the cell surface, it mimics a cell surface-bound antibody and provides a substrate for complement fixation.

In our assay, an antibody fusion protein that included the CH2 domain modified to include sialyl-Le$^X$ sites at amino acids #274 (K to N), # 287 (A to N), and #322 (K to N) was compared to an identical fusion protein lacking those sialyl-Le$^X$ addition sites. Results indicated that complement fixation was blocked by the presence of the sialyl-Le$^X$ moieties on the expressed antibody molecule. The extent of lysis exhibited by cells expressing the sialyl-$Le^X$-masked antibody molecule was less than that exhibited by cells expressing the control antibody molecule and was approximately equivalent to basal levels of cell lysis in the assay. Similar results were obtained in a separate set of analogous complement fixation experiments using antibody-CD4 fusion molecules (FIGS. 16A and 16B; SEQ ID NOS: 5 and 6). Deletion of the hinge region of IgG1 also created a molecule that was unrecognized by $F_c$ receptor and complement.

Based on the above, any number of recombinant $\alpha_1$-AGP-antibody fusion proteins may be designed having long plasma half-lives and the ability to inhibit undesirable cell-cell interactions (for example, the interactions between leukocytes and selectin-bearing cells). To generate molecules with heightened inhibitory potency, candidate molecules are designed and screened using the assays described above. In one particular example, molecules may be screened for their ability to incorporate sialyl-$Le^X$ and block the binding of neutrophils to activated endothelial cells; such molecules find use in the inhibition of selectin-dependent inflammatory reactions and tissue injury inflicted by invading leukocytes.

OTHER EMBODIMENTS

Other embodiments are within the claims. For example, the invention encompasses any antibody with decreased ability to fix complement and bind an $F_c$ receptor as a result of attached carbohydrate side chains; as described above, these include antibodies useful for their immunologic specificity (e.g., antibodies, e.g., MY904, Todd et al., U.S. Pat. No. 4,840,793) which competitively inhibit cell-cell interactions as well as antibodies which are used only as carriers for therapeutic carbohydrate groups. Because N-linked glycan addition sites are well known to be: Asparagine (N), X, Serine (S) or Threonine (T), where X stands for any residue except proline, one skilled in the art may design a molecule having any number of such sites and thus any number of carbohydrate side chains. Glycosylation sites are incorporated into the antibody sequence, for example, by in vitro site-directed mutagenesis.

Non-complement fixing and non-$F_c$ receptor binding antibodies would be used for purposes other than treating inflammation. For example, such an antibody directed against $GPII_bIII_a$ may be used to inhibit platelet aggregation and therefore would be useful for the treatment of myocardial infarction. Antibodies to proteins, such as fibrin or one of the clotting cascade proteins, would be useful for inhibiting thrombotic formation. In general, any antibody (including, without limitation, anti-Mo-1 and anti-CD14) proposed or demonstrated to have a therapeutic use may be improved by the addition of carbohydrate moieties which mask the antibody's ability to fix complement and bind an $F_c$ receptor. This characteristic would be particularly important, for example, for immunoglobulin fusion proteins such as IgG fusion proteins (see, for example, Seed et al., U.S. Ser. No. 08/483,151 entitled "Fucosyltransferase Genes and Uses Thereof," filed Jun. 7, 1995) and IgM fusion proteins (see, for example, Zettlemeisl et al., *DNA Cell Biol.* 9:347, 1990). In this case, a protein of interest is fused (for example, genetically) to an immunoglobulin molecule to increase the protein's serum half life. Because these fusion proteins have an extended life in the patient, they are more likely to be recognized as foreign antigens, and it is therefore particularly useful for such proteins to evade the patient's $F_c$ receptor binding and complement fixation systems.

For the purpose of blocking interactions between cells or proteins, any other appropriate carrier molecule may be utilized. Generally, proteins are preferred because of their relatively long half-lives in serum. One class of carrier proteins are serum proteins such as albumin (e.g., bovine serum albumin or human serum albumin), transferrin, or $\alpha$-2 macroglobulin. The carrier proteins can contain endogenous glycan addition sites or sites may be introduced into the DNA sequence of the carrier protein (as described above) by, for example, site-directed mutagenesis. The carrier molecule, less preferably, may be a lipid. In one example, the lipid, with one or more attached carbohydrate moieties (e.g., sialyl-$Le^X$ determinants), is delivered as a liposome to a target cell wall (e.g., an endothelial cell wall). The liposome may block a cell or protein interaction or may be used to deliver a drug to its appropriate site of action.

Cell adhesion molecules in addition to ELAM-1 may be inhibited by attachment of appropriate carbohydrate recognition moieties to a carrier molecule as described above. Such cell adhesion molecules may include, without limitation, LFA1, LFA-3, ICAM1, PADGEM, Mel14, LAM1, a cadherin, cell-CAM, or an N-CAM. Other glycans may be attached including, without limitation, any N-linked glycan, O-linked glycan, GMP140, Leu8, and phosphatidyl inositol phosphate glycans. In cases where the glycan addition signal is known, it may be introduced into the DNA sequence of an organic carrier molecule as described above. Alternatively, if the precise site is not known, but the general region of such an addition site in some naturally-occurring molecule has been defined, a DNA fragment (from the sequence encoding the naturally-occurring molecule) which includes that region may be cloned into the DNA sequence of the desired carrier molecule (e.g., an IgG1- or $\alpha_1$-AGP-encoding sequence).

Production of carrier molecules bearing carbohydrate moieties may be carried out in a cell, preferably, a eukaryotic cell other than yeast. Mammalian cells, e.g., mammalian cell lines, provide particularly suitable hosts. These cells generally synthesize the necessary precursor molecules and produce or can be engineered to produce the enzymes responsible for carbohydrate attachment. For the attachment of sialyl-$Le^X$ determinants, mammalian cell lines such as CHO and lec11 are particularly suitable. Alternatively, carbohydrate moieties may be attached to a carrier molecule in vitro, i.e., extracellularly. In one example, $\alpha(1,3)$ fucosyltransferase would be bound to a solid support (e.g., a column) and the desired carrier molecule passed over the bound fucosyltransferase enzyme, under conditions which facilitate attachment of sialyl-$Le^X$ groups to their appropriate site or the carrier molecule.

The invention also encompasses the use of sialyl-$Lewis^X$-modified $\alpha_1$-AGP-antibody fusion proteins for protecting against, inhibiting, or treating a shock-inducing event, the clinical manifestations of shock, or both which are caused by microbial factors (e.g., lipopolysaccharides (LPS)), microbial toxins (e.g., toxic shock enterotoxins), host mediators (e.g., cytokines), or anti-tumor therapies (e.g., administration of tumor necrosis factor (TNF) or interleukin1 (IL1)), or any combination thereof. For example, an $\alpha_1$-AGP antibody fusion protein can be administered to a human patient to alleviate the effects of septic shock induced by microbial LPS. The ability of an $\alpha_1$-AGP fusion protein to protect against, treat or inhibit the effects of shock (e.g., septicemia or toxic shock syndrome) is evaluated according to standard methods known in the art (e.g., those described in Libert et al. (1994) *J. Exp. Med.* 180: 1571–1575).

All publications, patents, and patent applications mentioned in this specification are herein incorporated by reference to the same extent as if each individual publication, patent, and patent application was specifically and individually indicated to be incoporated by reference.

In the claims:

1. A method of inhibiting the binding of a cell bearing an ELAM-1 protein to a molecule or cell bearing a sialyl-$Le^X$ determinant, comprising contacting said ELAM-1 bearing cell with an $\alpha_1$-acid glycoprotein (AGP)-antibody fusion protein bearing said sialyl-$Le^X$ determinant, wherein said inhibition of an ELAM-1-sialyl-$Le^X$-based interaction treats an adverse immune reaction.

2. The method of claim 1, wherein said AGP-antibody fusion protein comprises multiple said sialyl-$Le^X$ determinants.

3. The method of claim 1, wherein said antibody portion comprises an IgG1 CH2, CH3, or hinge domain.

4. The method of claim 1, wherein said antibody portion of said AGP-antibody fusion protein bears one or more non-naturally occurring sialyl-$Le^X$ determinants.

5. The method of claim 1, wherein the presence of said sialyl-$Le^X$ determinant on said AGP-antibody fusion protein interferes with said AGP-antibody fusion protein's ability to fix complement and bind an $F_c$ receptor.

6. The method of claim 5, wherein said sialyl-$Le^X$ determinant is attached to amino acid 269 of SEQ ID NO: 2.

7. The method of claim 5, wherein said sialyl-$Le^X$ determinant is attached to amino acid 282 of SEQ ID NO: 2.

8. The method of claim 5, wherein said sialyl-$Le^X$ determinant is attached to amino acid 317 of SEQ ID NO: 2.

9. The method of claim 5, wherein said AGP-antibody fusion protein is soluble.

10. The method of claim 5, wherein said sialyl-$Le^X$ determinant is attached to amino acid 290 of SEQ ID NO: 2.

11. The method of claim 5, wherein said sialyl-$Le^X$ determinant is attached to amino acid 330 of SEQ ID NO: 2.

* * * * *

UNITED STATES PATENT AND TRADEMARK OFFICE
CERTIFICATE OF CORRECTION

PATENT NO. : 6,613,746 B1
DATED : September 2, 2003
INVENTOR(S) : Seed et al.

It is certified that error appears in the above-identified patent and that said Letters Patent is hereby corrected as shown below:

Column 2,
Lines 5-6, "rhumatoid" should be -- rheumatoid --.

Column 4,
Line 61, "subsituting" should be -- substituting --.

Column 5,
Line 41, "therefor" should be -- therefore --;
Line 64, "supernantant" should be -- supernatant --.

Column 13,
Line 34, "muations" should be -- mutations --.

Column 18,
Line 8, "incoporated" should be -- incorporated --.

Signed and Sealed this

Twenty-first Day of September, 2004

JON W. DUDAS
*Director of the United States Patent and Trademark Office*